(12) United States Patent
Schabbach et al.

(10) Patent No.: US 11,666,705 B2
(45) Date of Patent: Jun. 6, 2023

(54) MEDICAMENT DELIVERY DEVICE

(71) Applicant: Sanofi-Aventis Deutschland GMBH, Frankfurt am Main (DE)

(72) Inventors: Michael Schabbach, Frankfurt am Main (DE); Beate Franke, Frankfurt am Main (DE); Giuliano Pradel, Besana in Brianza (IT); Ilario Melzi, Milan (IT); Stefan Verlaak, Paderno d'Adda (IT); Andrew Nelson, Dallas, TX (US)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 531 days.

(21) Appl. No.: 16/336,266

(22) PCT Filed: Sep. 20, 2017

(86) PCT No.: PCT/EP2017/073722
§ 371 (c)(1),
(2) Date: Mar. 25, 2019

(87) PCT Pub. No.: WO2018/060024
PCT Pub. Date: Apr. 5, 2018

(65) Prior Publication Data
US 2019/0224414 A1 Jul. 25, 2019

(30) Foreign Application Priority Data
Sep. 27, 2016 (EP) .................. 16190881

(51) Int. Cl.
*A61M 5/20* (2006.01)
*A61M 5/28* (2006.01)
(Continued)

(52) U.S. Cl.
CPC .......... *A61M 5/2033* (2013.01); *A61M 5/148* (2013.01); *A61M 5/14248* (2013.01);
(Continued)

(58) Field of Classification Search
CPC ............ A61M 5/2033; A61M 5/14248; A61M 5/148; A61M 5/282; A61M 5/283;
(Continued)

(56) References Cited

U.S. PATENT DOCUMENTS

| 6,626,329 | B2 * | 9/2003 | Rake | A61M 5/148 |
| | | | | 128/DIG. 12 |
| 7,686,788 | B2 * | 3/2010 | Freyman | A61M 5/14593 |
| | | | | 604/99.01 |

(Continued)

FOREIGN PATENT DOCUMENTS

| CN | 1218413 | 6/1999 |
| CN | 2429179 | 5/2001 |

(Continued)

OTHER PUBLICATIONS

International Preliminaiy Report on Patentability in International Application No. PCT/EP2017/073722, dated Apr. 2, 2019, 8 pages.

(Continued)

*Primary Examiner* — Quynh-Nhu H. Vu
(74) *Attorney, Agent, or Firm* — Fish & Richardson P.C.

(57) ABSTRACT

The present disclosure relates to a medicament delivery device comprising a housing, a reservoir for medicament disposed in the housing and a dispensing member. The dispensing member is moveable relative to the housing from a first position to a second position to dispense medicament from the reservoir when the reservoir contains medicament. The medicament delivery device further comprises first and second biasing members. The first biasing member is configured to urge the dispensing member from the first position
(Continued)

to an intermediate position. The second biasing member is configured to urge the dispensing member from the intermediate position to the second position.

17 Claims, 10 Drawing Sheets

(51) Int. Cl.
| | | |
|---|---|---|
| A61M 5/32 | (2006.01) | |
| A61M 5/142 | (2006.01) | |
| A61M 5/148 | (2006.01) | |
| A61M 5/315 | (2006.01) | |
| A61M 5/145 | (2006.01) | |

(52) U.S. Cl.
CPC ............ *A61M 5/282* (2013.01); *A61M 5/283* (2013.01); *A61M 5/322* (2013.01); *A61M 2005/14256* (2013.01); *A61M 2005/14272* (2013.01); *A61M 2005/14506* (2013.01); *A61M 2005/2073* (2013.01); *A61M 2005/31518* (2013.01)

(58) Field of Classification Search
CPC ........ A61M 5/322; A61M 2005/14272; A61M 2005/14256; A61M 2005/14506; A61M 2005/2073; A61M 2005/31518
See application file for complete search history.

(56) References Cited

U.S. PATENT DOCUMENTS

| | | | |
|---|---|---|---|
| 2002/0022798 A1 | 2/2002 | Connelly et al. | |
| 2002/0123741 A1 | 9/2002 | Rake et al. | |
| 2003/0167041 A1* | 9/2003 | Rosoff | A61M 5/282 604/232 |
| 2013/0035634 A1* | 2/2013 | Cappello | A61M 5/30 604/68 |
| 2013/0197475 A1* | 8/2013 | Dunn | A61M 5/326 604/506 |
| 2014/0046259 A1* | 2/2014 | Reber | A61M 5/2033 604/136 |
| 2014/0114248 A1* | 4/2014 | DeSalvo | A61M 5/16877 604/140 |
| 2014/0200510 A1* | 7/2014 | Agard | A61M 5/3157 604/152 |
| 2015/0258283 A1* | 9/2015 | Imai | A61M 5/31501 604/195 |
| 2016/0243310 A1* | 8/2016 | Dasbach | A61M 5/31513 |

FOREIGN PATENT DOCUMENTS

| | | | |
|---|---|---|---|
| CN | 102497909 | 6/2012 | |
| CN | 102665800 | 9/2012 | |
| CN | 102858392 | 1/2013 | |
| CN | 103249443 | 8/2013 | |
| CN | 103370091 | 10/2013 | |
| CN | 103492000 | 1/2014 | |
| CN | 104689426 | 6/2015 | |
| CN | 104906663 | 9/2015 | |
| CN | 105682707 | 6/2016 | |
| GB | 2229636 A * | 10/1990 | ......... A61M 5/1417 |
| JP | 2001-513657 | 9/2001 | |
| JP | 2013-523202 | 6/2013 | |
| JP | 2014-500090 | 1/2014 | |
| JP | 2016-504164 | 2/2016 | |
| WO | WO 97/34651 | 9/1997 | |
| WO | WO 2011/014514 | 2/2011 | |
| WO | WO 2011/048422 | 4/2011 | |
| WO | WO 2011/117592 | 9/2011 | |
| WO | WO 2012/045831 | 4/2012 | |
| WO | WO 2012/073035 | 6/2012 | |
| WO | WO 2012/110572 | 8/2012 | |
| WO | WO 2012/140097 | 10/2012 | |
| WO | WO 2014/009706 | 1/2014 | |
| WO | WO 2014/116987 | 7/2014 | |
| WO | WO 2015/055588 | 4/2015 | |
| WO | WO 2016/027096 | 2/2016 | |
| WO | WO-2016107789 A1 * | 7/2016 | ......... A61M 5/2033 |

OTHER PUBLICATIONS

International Search Report and Written Opinion in International Application No. PCT/EP2017/073722, dated Nov. 30, 2017, 12 pages.

* cited by examiner

MEDICAMENT DELIVERY DEVICE

CROSS REFERENCE TO RELATED APPLICATIONS

The present application is the national stage entry of International Patent Application No. PCT/EP2017/073722, filed on Sep. 20, 2017, and claims priority to Application No. EP 16190881.9, filed on Sep. 27, 2016, the disclosures of which are incorporated herein by reference.

TECHNICAL FIELD

The present disclosure relates to a medicament delivery device.

BACKGROUND

A variety of diseases exist that require regular treatment by injection of a medicament and such injections can be performed by using injection devices. Various injection devices for delivering injections of medicament are known in the art. Another type of injection pump that is gaining traction is the bolus injector device. Some bolus injector devices are intended to be used with relatively large volumes of medicament, typically at least 1 ml and maybe a few ml. Injection of such large volumes of medicament can take some minutes or even hours. Such high capacity bolus injector devices can be called large volume devices (LVDs). Generally such devices are operated by the patients themselves, although they may also be operated by medical personnel.

SUMMARY

It is an object of the present disclosure to provide an improved medicament delivery device.

According to the present disclosure, there is provided a medicament delivery device comprising: a housing; a reservoir for medicament disposed in the housing; a dispensing member that is moveable relative to the housing from a first position to a second position to dispense medicament from the reservoir when the reservoir contains medicament; a first biasing member configured to urge the dispensing member from the first position to an intermediate position; and, a second biasing member configured to urge the dispensing member from the intermediate position to the second position.

The length of the medicament delivery device in the direction that the first and second biasing members urge the dispensing member can therefore be made smaller in comparison to a medicament delivery device that only comprises a single biasing member. This is because the length of each of the first and second biasing members can be made smaller than said single biasing member to achieve the same total displacement of the dispensing member within the housing. The first and second biasing members may be arranged in the housing such that they take up less space than said single biasing member in the direction that the first and second biasing members urge the dispensing member.

In some embodiments, the first and second biasing members have different characteristics such that the movement of the dispensing member from the first position to the intermediate positon is different to the movement of the dispensing member from the intermediate position to the second position.

In one embodiment, the first and second biasing members share a common axis. One of the first and second biasing members may be disposed inside the other one of the first and second biasing members when the dispensing member is in the first position. The first and second biasing members may be arranged in a telescopic configuration.

In one embodiment, the first and/or second biasing member comprises a spring. The first and second biasing members may comprise springs having different spring constants. Therefore, movement of the dispensing member from the first position to the intermediate positon is different to the movement of the dispensing member from the intermediate position to the second position. The first spring may have a greater or smaller spring constant than the second spring.

In one embodiment, the medicament delivery device further comprises a first lock moveable from a locked state to an unlocked state to allow movement of the dispensing member from the first position to the intermediate position and/or a second lock moveable from a locked state to an unlocked state to allow movement of the dispensing member from the intermediate position to the second position. The second lock may be configured such that movement of the dispensing member from the first position to the intermediate position causes the second lock to move to the unlocked state. Thus, the patient does not need to manually operate the second lock to commence movement of the dispensing member from the intermediate position to the second position.

In one embodiment, the second biasing member is displaced relative to the first biasing member in the direction of motion of the dispensing member when the dispensing member moves from the first position to the intermediate position.

In one embodiment, the first and second biasing members are telescopically arranged within the housing. This reduces the size of the medicament delivery device such that the medicament delivery device is easier to transport and store.

In one embodiment, the medicament delivery device further comprises an extension member, wherein the second biasing member is disposed between a first side of the extension member and the dispensing member, and wherein the first biasing member is disposed on a second side of the extension member. The first biasing member may be configured to exert a force on said second side of the extension member to urge the dispensing member from the first position to the intermediate position.

In one embodiment, the extension member is configured to be urged against the dispensing member. The extension member may be urged against the dispensing member to move the dispensing member from the first position to the intermediate position.

In one embodiment, the needle is movable from a retracted position, wherein the needle is fully disposed within the housing, to an extended position, wherein the needle projects from the housing. In one such embodiment, the needle enters an injection site of the patient when the medicament delivery device is applied to the injection site and the needle is moved from the retracted position to the extended position. Thus, the patient does not need to manually insert the needle into the injection site. The needle may be coupled to the dispensing member such that movement of the dispensing member from the first position to the intermediate position moves the needle from the retracted position to the extended position.

In one embodiment, the first biasing member is configured to exert a larger force on the displacement member than the second biasing member. Therefore, the force to move the needle from the retracted position to the extended position is greater than the force exerted on the dispensing member to dispense medicament from the reservoir. Alternatively, the first biasing member may be configured to exert a smaller force on the displacement member than the second biasing member such that the force exerted to move the needle from the retracted position to the extended position is smaller than the force exerted on the dispensing member to dispense medicament from the reservoir.

In one embodiment, the dispensing member is moveable relative to the housing from the first position to the intermediate position to dispense medicament from the reservoir and is movable from the intermediate position to the second position to dispense further medicament from the reservoir when the reservoir contains medicament. In one such embodiment, the rate of the delivery of medicament during movement of the dispensing member from the first position to the intermediate positon may be different, for example, greater or smaller, than the rate of delivery during movement of the dispensing member from the intermediate position to the second position. In one embodiment, the first biasing member is configured to exert a larger force on the displacement member than the second biasing member. Therefore, the rate of drug delivery is initially greater, during movement of the displacement member from the first position to the intermediate position, than during subsequent movement of the displacement member from the intermediate position to the second position. Alternatively, the second biasing member may be configured to exert a larger force on the displacement member than the first biasing member.

In one embodiment, the extension member remains stationary relative to the dispensing member when the dispensing member moves from the first position to the intermediate position.

In one embodiment, the reservoir contains medicament. The reservoir comprises a collapsible container. The reservoir may be a flexible bag. The reservoir may comprise a telescopically collapsible container. In one embodiment, the collapsible container comprises a bellows.

The dispensing member may comprise a flat plate.

In one embodiment, the dispensing member comprises first and second sides, wherein the first and second biasing members are disposed on the first side of the dispensing member and the reservoir is disposed on the second side of the dispensing member.

In one embodiment, the housing comprises a distal end, which may have an adhesive layer.

The medicament delivery device may be a large volume device.

According to the present disclosure, there is also provided a method of dispensing medicament from a medicament delivery device that has a housing, a reservoir disposed in the housing, a dispensing member and first and second biasing members, the method comprising: releasing the first biasing member to exert a force on the dispensing member to move the dispensing member from a first position to an intermediate position; and, then, releasing the second biasing member to exert a force on the dispensing member to move the dispensing member from the intermediate position to a second position to dispel medicament from the reservoir.

The medicament delivery device may have any of the features described above and, for example, the reservoir may comprise a collapsible container.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying drawings, in which.

DETAILED DESCRIPTION

Figure 1:
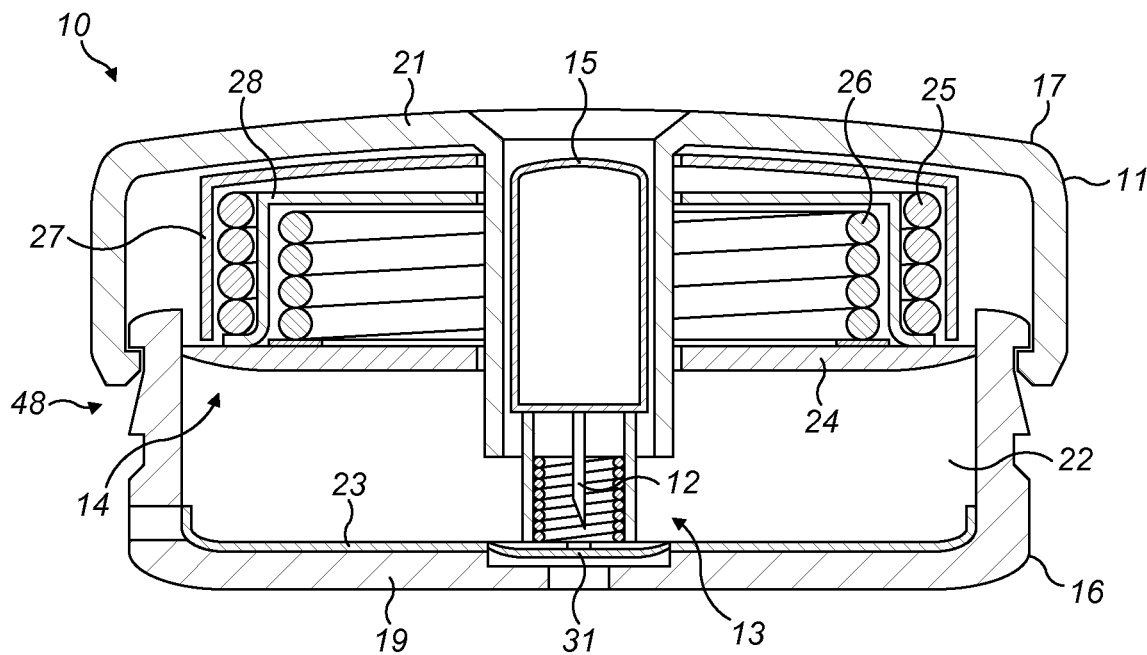
FIG. 1 is a schematic cross-sectional side view of a medicament delivery device according to a first embodiment of the disclosure, wherein a proximal portion of the housing is in an initial position and a flexible bag is empty.

A medicament delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for a large volume device). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

FIGS. 1 to 9B show a medicament delivery device 10, which in the exemplary embodiment comprises a bolus injector device, according to a first embodiment of the disclosure. The medicament delivery device 10 may be in the form of a large volume device.

The medicament delivery device 10 comprises a housing 11, a needle 12, and a medicament delivery mechanism comprising a needle actuating mechanism 13 and a dispensing mechanism 14. The medicament delivery device 10 further comprises an actuator 15.

The housing 11 comprises a distal portion 16 and a proximal portion 17. The term "distal" refers to a location that is relatively closer to a site of injection and the term "proximal" refers to a location that is relatively further away from the injection site.

The distal portion 16 of the housing 11 comprises a cylindrical peripheral wall 18 and an end wall 19 that together have a generally U-shaped cross-section. The distal portion 16 of the housing 11 further comprises a cylindrical internal wall 16A that is arranged concentrically with the cylindrical peripheral wall 18 of the distal portion 16. The proximal portion 17 of the housing 11 comprises a cylindrical peripheral wall 20 and an end wall 21 that together have a generally U-shaped cross-section. The proximal portion 17 of the housing 11 comprises a cylindrical internal wall 17A that is arranged concentrically with the cylindrical peripheral wall 20 of the proximal portion 17.

The peripheral wall 18 of the distal portion 16 of the housing 11 is slidably received in the peripheral wall 20 of the proximal portion 17 such that the end wall 19 of the distal portion 16 is spaced from the end wall 21 of the proximal portion 17 and a recess 22 is formed therebetween. The distal and proximal portions 16, 17 of the housing 11 together form a generally cylindrical shape that has a central axis (see the dashed line A-A in FIG. 2).

The end wall 19 of the distal portion 16 has an outer surface 19A and an inner surface 19B and the end wall 21 of the proximal portion 17 has an outer surface 21A and an inner surface 21B. One or both of the outer surfaces 19A, 21A of the end walls 19, 21 of the distal and proximal portions 16, 17 may be substantially flat.

The outer surface 19A of the end wall 19 of the distal portion 16 comprises an adhesive layer (not shown) that is initially covered by a label (not shown). In use, the label is removed from the adhesive layer and then the adhesive layer is stuck to the patient's skin at the injection site of the patient such that the end wall 19 of the distal portion 16 is adhered to the injection site.

The dispensing mechanism 14 comprises a medicament reservoir 23, a dispensing member 24, first and second biasing members 25, 26, and first and second dispensing locks (not shown).

The medicament reservoir 23 is in the form of an annular flexible bag 23. The flexible bag 23 is disposed in the recess 22 in the housing 11 and abuts the inner surface 19B of the end wall 19 of the distal portion 16. The flexible bag 23 is fluidly connected to an aperture 18A in the peripheral wall 18 of the distal portion 16. The aperture 18A forms a filling port 18A that allows for the flexible bag 23 to be filled with medicament through the peripheral wall 18 of the distal portion 16. The flexible bag 23 and/or the aperture 18A may comprise a one-way valve (not shown) that is configured to prevent medicament from flowing out of the flexible bag 23 via the aperture 18A. Alternatively, or additionally, a bung (not shown) may be provided that is inserted into the aperture 18A to seal the aperture 18A after the flexible bag 23 has been filled with medicament.

The dispensing member 24 is in the form of a plate 24. The plate 24 may be annular. The plate 24 is disposed in the recess 22 in the housing 11 such that the flexible bag 23 is located between a distal-facing surface 24A of the plate 24 and the inner surface 19B of the end wall 19 of the distal portion 16. The plate 24 is slidable in the recess 22 in the direction of the central axis A-A of the housing 11 such that the plate 24 is moveable relative to flexible bag 23.

The first and second biasing members 25, 26 are in the form of respective first and second springs 25, 26. The first spring 25 and/or second spring 26 may be a helical spring.

The dispensing mechanism 14 further comprises an internal container 27 and an extension member 28. The internal container 27 comprises an end wall 27A and a peripheral wall 27B which may be integrally formed. The end wall 27A of the internal container 27 is located at the proximal end of the peripheral wall 27B. The end wall 27A of the internal container 27 is secured to the end wall 21 of the proximal portion 17 of the housing 11 or may be in abutment or integrally formed therewith. The peripheral wall 27B of the internal container 27 is generally cylindrical and is arranged concentrically with the cylindrical peripheral wall 20 of the proximal portion 17. The peripheral wall 27B of the internal container 27 is disposed between the peripheral wall 20 and the internal wall 17A of the proximal portion 17.

The extension member 28 is disposed in the recess 22 in the housing 11 and is moveable relative to the housing 11 in the direction of the central axis A-A of the housing 11.

The extension member 28 comprises a first portion 28A, an intermediate portion 28B and a second portion 28C. The first portion 28A is in the form of an end wall 28A. The intermediate portion 28B is in the form of a peripheral wall 28B. The second portion 28C is in the form of a lip 28C.

The end wall 28A of the extension member 28 is spaced from the lip 28C in the direction of the central axis A-A of the housing 11 such that the end wall 28A is located nearer than the lip 28C to the end wall 21 of the proximal portion 17. The end wall 28A extends radially inwardly from the proximal end of the peripheral wall 28B of the extension member 28 towards the internal wall 17A of the proximal portion 17.

The peripheral wall 28B of the extension member 28 is generally cylindrical and is arranged concentrically between the peripheral walls 18, 20 of the distal and proximal portions 16, 17 of the housing 11.

The lip 28C extends radially outwardly from the distal end of the peripheral wall 28B of the extension member 28. A distal-facing surface of the lip 28C abuts the plate 24.

The first spring 25 is disposed in the recess 22 in the housing 11 on the opposite side of the plate 24 to the flexible bag 23. The first spring 25 extends about the peripheral axis A-A of the housing 11. More specifically, the first spring 25 is located between the peripheral wall 27B of the internal container 27 and the peripheral wall 28B of the extension member 28.

A proximal end of the first spring 25 abuts the end wall 27A of the internal container 27 and a distal end abuts a proximal-facing surface of the lip 28C. Thus, the first spring 25 is configured to urge the extension member 28 away from the end wall 21 of the proximal portion 17, which is attached to the internal container 27, in the direction of the central axis A-A of the housing 11 such that the extension member 28 is urged towards the end wall 19 of the distal portion 16.

The second spring 26 is disposed in the recess 22 in the housing 11 on the opposite side of the plate 24 to the flexible bag 23. The second spring 26 extends about the peripheral axis A-A of the housing 11. More specifically, the second spring 26 is located between the peripheral wall 28B of the extension member 28 and the internal wall 17A of the proximal portion 17. Thus, initially, the second spring 26 is located inside the first spring 25. The first and second springs 25, 26 may share a common axis A-A.

A proximal end of the second spring 26 abuts the end wall 28A of the extension member 28 and a distal end abuts a proximal-facing surface 24B of the plate 24. Thus, the second spring 26 is configured to urge the plate 24 away from the end wall 28A of the extension member 28 in the direction of the central axis A-A of the housing 11 such that the plate 24 is urged towards the end wall 19 of the distal portion 16.

The first dispensing lock is moveable from a locked state to an unlocked state. When the first dispensing lock is in the locked state, the extension member 28 is fixed relative to the proximal portion 17 of the housing 11 in the direction of the central axis A-A of the housing 11 such that the extension member 28 is retained in position in the inner container 27. When the first dispensing lock is in the unlocked state, the extension member 28 is able to move relative to the proximal portion 17 to move away from the end wall 27A of the inner container 27 in the direction of the central axis A-A of the housing 11.

The second dispensing lock is moveable from a locked state to an unlocked state. When the second dispensing lock is in the locked state, the plate 24 is fixed relative to the extension member 28 in the direction of the central axis A-A of the housing 11 such that the plate 24 is held against the distal-facing surface of the lip 28C. When the second dispensing lock is in the unlocked state, the plate 24 is able to move relative to the extension member 28 to move away from the end wall 28A of the extension member 28 in the direction of the central axis A-A of the housing 11.

The proximal portion 17 is moveable relative to the distal portion 16 of the housing 11 between an initial position (shown in FIGS. 1 and 2) and a primed position (shown in FIGS. 3, 4, and 6 to 8). When the proximal portion 17 is in the initial position, the end wall 21 of the proximal portion 17 is spaced from the end wall 19 of the distal portion 16 such that the plate 24 is spaced from the flexible bag 23. Furthermore, when the proximal portion 17 is in the initial position, only a small section of the peripheral wall 18 of the distal portion 16 is received in the peripheral wall 20 of the proximal portion 17.

When the proximal portion 17 is moved to the primed position, the end wall 21 of the proximal portion 17 is moved towards the end wall 19 of the distal portion 16 such that the distance between the end walls 19, 21 is reduced. This causes the plate 24 to move to abut the flexible bag 23. An increased amount of the peripheral wall 18 of the distal portion 16 is received in the peripheral wall 20 of the proximal portion 17 when the proximal portion 17 is in the primed position.

The actuator 15 is in the form of a button 15 that has a peripheral wall 15A and an end wall 15B. The button 15 is received in the proximal portion 17 of the housing 11 such that the peripheral wall 15A of the button 15 is located on the inside of the internal wall 17A of the proximal portion 17 and is concentrically aligned therewith. The button 15 is slidable within the internal wall 17A of the proximal portion 17 in the direction of the central axis A-A of the housing 11.

The needle 12 is moveable relative to the distal portion 16 of the housing 11 between a retracted position (shown in FIGS. 1 to 3, 8 and 9B) and an extended position (shown in FIGS. 4, 6, 7 and 9A). When the needle 12 is in the retracted position, the needle 12 is fully received in the recess 22 in the housing 11 such that the needle 12 is shielded to prevent damage to the needle 12 and to protect the patient from being accidentally injured by the needle 12.

When the needle 12 is moved from the retracted position to the extended position, the needle 12 is moved linearly in the direction of the central axis A-A of the housing 11 such that the end of the needle 12 projects out of an aperture 19C in the end wall 19 of the distal portion 16. Thus, when the adhesive layer of the distal portion 16 is adhered to the injection site of a patient, the needle 12 pierces the patient's skin to extend into the injection site to deliver medicament thereto.

The medicament delivery device 10 further comprises a septum 31 that is fixed to the inner surface 19B of the end wall 19 of the distal portion 16. The septum 31 is located over the aperture 19C in the end wall 19 of the distal portion 16. The needle 12, which is initially in the retracted position, is protected by the septum 31. More specifically, the septum 31 prevents the ingress of contaminants through the aperture 19C in the end wall 19 of the distal portion 16 and into contact with the sterile needle 12. When the needle 12 is moved to the extended position, the needle 12 pierces the septum 31 and the end of the needle 12 passes through the septum 31 to project from the end wall 19. The septum 31 may be manufactured from an impermeable material such as plastic, rubber or metal foil. In alternative embodiments, the septum 31 is fixed to the outer surface 19A of the end wall 19 of the distal portion 16 or is located in the aperture 19C in the end wall 19.

The needle actuating mechanism 13 comprises needle extension and retraction biasing members 32, 33, extension and retraction holding elements 34, 35, and needle extension and retraction locks 36, 37.

The needle extension biasing member 32 is in the form of a needle extension spring 32. The needle extension spring 32 may be a helical spring. The needle extension spring 32 is located inside the peripheral wall 15A of the button 15 and extends about the central axis A-A of the housing 11. The needle extension spring 32 is disposed between a base 12A of the needle 12 and the extension holding element 34.

The extension holding element 34 is fixed relative to the distal portion 16 of the housing 11 and is located on the opposite side of the base 12A of the needle 12 to the septum 31. The extension holding element 34 is configured to act as a stop against which the proximal end of the needle extension spring 32 abuts such that the proximal end of the needle extension spring 32 is prevented from moving towards the end wall 21 of the proximal portion 17 in the direction of the central axis A-A of the housing 11. When the needle 12 is in the initial retracted position, the needle extension spring 32 is compressed between the base 12A of the needle 12 and the extension holding element 34 such that the needle extension spring 32 urges the needle 12 away from the extension holding element 34 in the direction of the central axis A-A of the housing 11 such that the needle 12 is biased to move into the extended position.

The needle extension lock 36 comprises an extension locking member 38 that is connected to the distal portion 16 of the housing 11 by a pivotal coupling 39. The extension locking member 38 comprises an elongate member 38A and first and second projections 40, 41 that are integrally formed with the elongate member 38A. The first projection 40 is located at the distal end of the elongate member 38A and the second projection 41 is located towards the proximal end of the elongate member 38A.

The elongate member 38A is attached to the pivotal coupling 39 at a point between the proximal and distal ends of the elongate member 38A such that the first and second projections 40, 41 are pivotable about the pivotal coupling 39.

Figure 5:
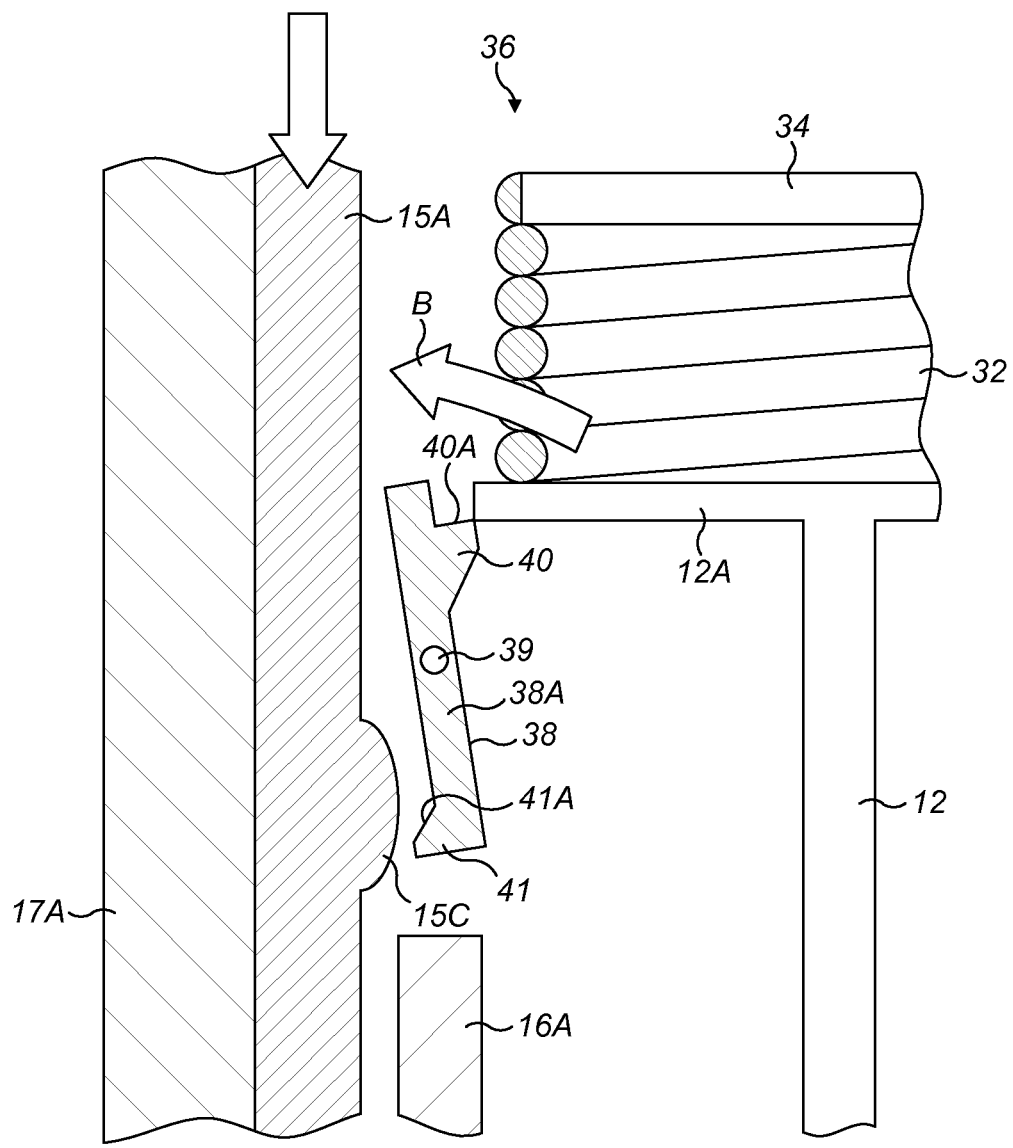
FIG. 5 is a close-up schematic cross-sectional side view of a needle extension lock of the medicament delivery device of FIG. 1, wherein a needle locking members is moved to an unlocked state.

The extension locking member 38 is moveable from a locked state to an unlocked state (as shown in FIG. 5). In the locked state, the extension locking member 38 is positioned such that the elongate member 38A extends substantially parallel to the central axis A-A of the housing 11 and the first projection 40 is located nearer to the end wall 21 of the proximal portion 17 than the second projection 41.

The first projection 40 of the extension locking member 38 extends radially inwardly towards the central axis A-A of the housing 11 when the extension locking member 38 is in the locked state.

The first projection 40 comprises a proximal-facing surface 40A that abuts the base 12A of the needle 12 when the extension locking member 38 is in the locked state such that movement of the needle 12 in the direction of the central axis A-A of the housing 11 towards the end wall 19 of the distal portion 16 is prevented. Thus, when the extension locking member 38 is in the locked state, the extension locking member 38 retains the needle 12 in the retracted position against the force of the needle extension spring 32, which is held in a compressed state between the base 12A of the needle 12 and the extension holding element 34.

The second projection 41 of the extension locking member 38 extends radially outwardly away from the central axis A-A of the housing 11 when the extension locking member 38 is in the locked state. The second projection 41 comprises an angled surface 41A that faces at an angle away from the central axis A-A of the housing 11 and towards the end wall 21 of the proximal portion 17.

The button 15 comprises a lip 15C that extends radially inwardly from the inside of the peripheral wall 15A of the button 15 in the direction towards the central axis A-A of the housing 11. The lip 15C may be generally annular.

The lip 15C of the button 15 is configured to abut the angled surface 41A of the extension locking member 38 when the button 15 is moved within the housing 11 towards the end wall 19 of the distal portion 16. This causes the second projection 41 of the extension locking member 38 to be urged radially inwardly towards the central axis A-A such that the extension locking member 38 is rotated from the locked state to the unlocked state (in the direction of arrow 'B' in FIG. 5). In the unlocked state, the first projection 40 is moved radially outwardly such that it no longer abuts the base 12A of the needle 12 and therefore the base 12A of the needle 12 is able to move away from the extension holding element 34 under the force of the needle extension spring 32. Thus, when the extension locking member 38 is moved to the unlocked state the needle 12 moves from the retracted position to the extended position under the force of the needle extension spring 32.

The needle retraction biasing member 33 is in the form of a needle retraction spring 33. The needle retraction spring 33 may be a helical spring. The needle retraction spring 33 is located inside the distal portion 16 of the housing 11 and extends about the central axis A-A thereof. The needle retraction spring 33 is disposed between the retraction holding element 35 and the septum 31. The septum 31 is fixed relative to the distal portion 16 of the housing 11 and therefore acts as a stop against which the distal end of the needle retraction spring 33 abuts.

The retraction holding element 35 is slidably received in the internal wall 16A of the distal portion 16 of the housing 11. The needle retraction spring 33 is initially compressed between the septum 31 and the retraction holding element 35 such that the needle retraction spring 33 urges the retraction holding element 35 away from the septum 31 in the direction of the central axis A-A of the housing 11. The needle retraction lock 37 initially retains the retraction holding element 35 in position against the force of the needle retraction spring 33 such that the needle retraction spring 33 is compressed.

The needle retraction lock 37 comprises a retraction locking member 42 that is connected to the distal portion 16 of the housing 11 by a pivotal coupling 43. The retraction locking member 42 comprises first and second elongate members 44, 45, a recess 46, and a projection 47. The first and second elongate members 44, 45 are integrally formed at one end. The first and second elongate members 44, 45 extend at an angle to each other. In the present embodiment, the first and second elongate members 44, 45 extend substantially perpendicular to each other.

The first and second elongate members 44, 45 comprise respective free ends 44A, 45B that are remote to the pivotal coupling 43. The recess 46 is located at the free end 44A of the first elongate member 44 and the projection 47 is located at the free end 45A of the second elongate member 45.

Figure 9A:
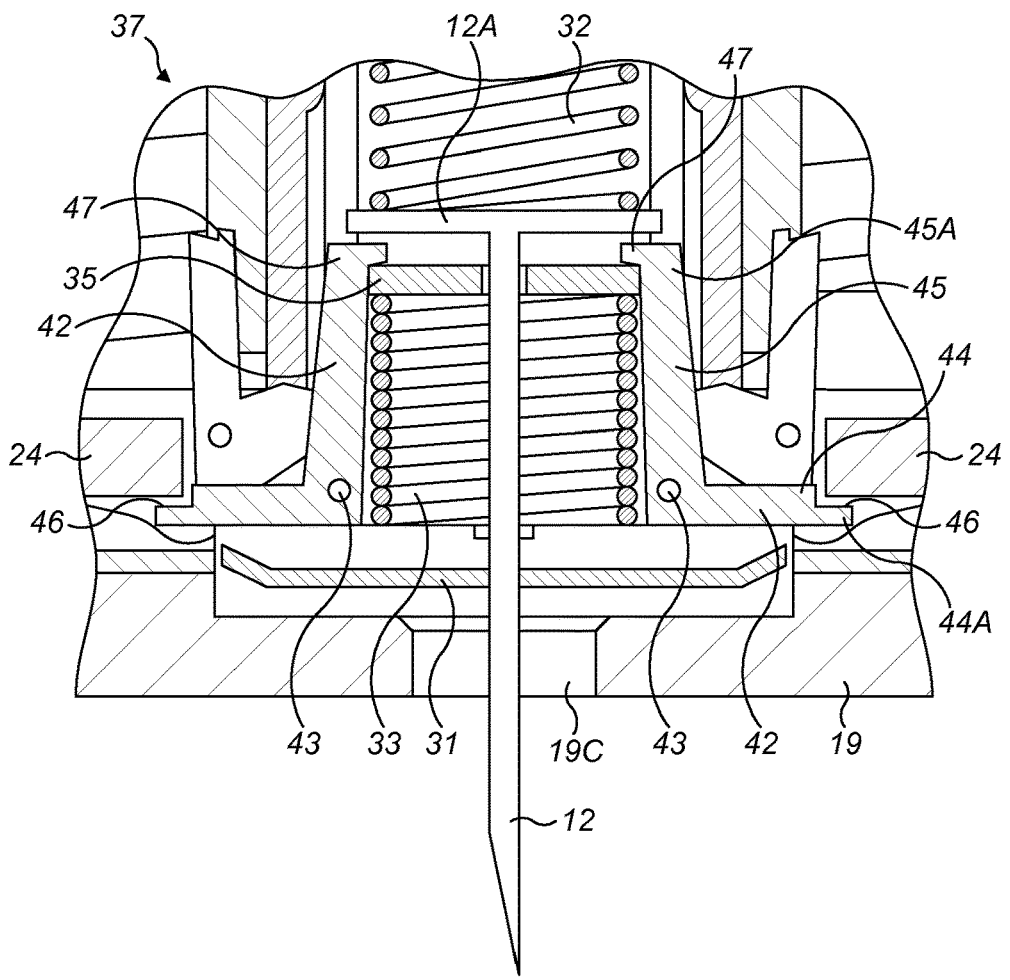
FIG. 9A is a close-up schematic cross-sectional side view of a needle retraction lock of the medicament delivery device of FIG. 1, wherein a pair of retraction locking members are in a locked state.
Figure 9B:
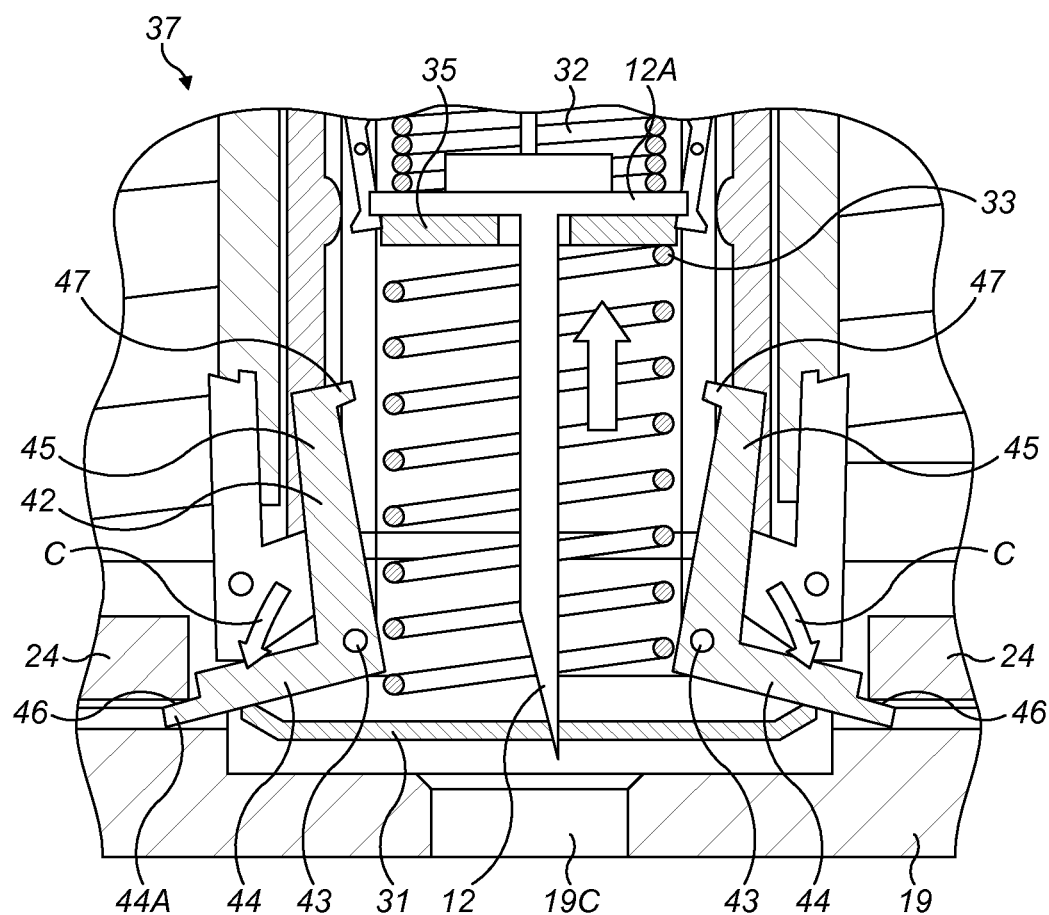
FIG. 9B is a close-up schematic cross-sectional side view of the needle retraction lock of the medicament delivery device of FIG. 1, wherein the pair of retraction locking members are in an unlocked state.

The retraction locking member 42 is pivotable from a locked state (shown in FIG. 9A) to an unlocked state (shown in FIG. 9B). In the locked state, the retraction locking member 42 is positioned such that the first elongate member 44 extends radially outwardly away from the central axis A-A of the housing 11 and, in one embodiment, is substantially perpendicular to the central axis A-A of the housing 11.

The free end 44A of the first elongate member 44 overlaps the plate 24 in the radial direction. Moreover, in the locked state, the retraction locking member 42 is positioned such that the second elongate members 45 extend towards the end wall 21 of the proximal portion 17 from the pivotal coupling 43 and, in one embodiment, is substantially parallel to the central axis A-A of the housing 11.

When the retraction locking member 42 is in the locked state, the projection 47 extends radially inwardly towards the central axis A-A of the housing 11 to abut a proximal-facing surface of the retraction holding element 35. Thus, the retraction holding element 35 is prevented from moving towards the end wall 21 of the proximal portion 17 and thus the needle retraction spring 33 is held in a compressed state between the septum 31 and the retraction holding element 35.

Movement of the plate 24 within the housing 11 towards the end wall 19 of the distal portion 16, due to operation of the dispensing mechanism 14, causes the plate 24 to be urged against the free end 44A of the first elongate member 44 such that the plate 24 is received in the recess 46 of the first elongate member 44. Thus, the movement of the plate 24 towards the end wall 19 of the distal portion 16 results in a force being exerted on the free end 44A of the first elongate member 44. This force causes the free end 44A of the first elongate member 44 to be urged towards the end wall 19 of the distal portion 16 such that the retraction locking member 42 is urged to rotate about the pivotal coupling 43 from the locked state to the unlocked state (in the direction of arrow 'C' in FIG. 9B).

When the retraction locking member 42 is rotated to the unlocked state, the projection 47 at the free end 45A of the second elongate member 45 is moved radially outwardly away from the central axis A-A of the housing 11 such that the projection 47 is spaced from the retraction holding element 35. Thus, the projection 47 no longer holds the retraction holding element 35 in place against the force of the needle retraction spring 33 and so the retraction holding element 35 is moved towards the end wall 21 of the proximal end 17 by the needle retraction spring 33.

The needle 12 extends through an aperture 35A in the retraction holding element 35 such that when the needle 12 is in the extended position and the retraction locking member 42 is in the locked state (as shown in FIG. 9A) the base 12A of the needle 12 is located in proximity to the retraction holding element 35. Thus, when the retraction locking member 42 is subsequently moved to the unlocked state, the retraction holding element 35 is released such that the needle retraction spring 33 urges the retraction holding element 35 against the base 12A of the needle 12 to move the needle 12 towards the end wall 21 of the proximal portion 17 and into the retracted position (as shown in FIG. 9B).

A clearance gap (not shown) may be provided between the retraction locking member 42 and the septum 31 and end wall 19 of the distal portion 16 to facilitate movement of the retraction locking member 42 between the locked and unlocked states. Alternatively, the septum 31 may be manufactured from a flexible material that facilitates movement of the retraction locking member 42.

The medicament delivery device 10 further comprises a coupling 48 between the distal and proximal portions 16, 17 of the housing 11. The coupling 48 is configured to resist the proximal portion 17 from being moving away from the primed position towards the initial position. The coupling 48 may be configured to prevent the force of the first and second springs 25, 26, which are located between the plate 24 and the end wall 21 of the proximal portion 17, from moving the end wall 21 of the proximal portion 17 away from the end wall 19 of the distal portion 16 when the proximal portion 17 is in the primed position and, for example, the first and second dispensing locks are moved to the unlocked state.

The coupling 48 is in the form of a latch 48. The latch 48 comprises first, second and third stops 49, 50, 51. The first stop 49 is in the form of a first lip 49 that is integrally formed with the peripheral wall 20 of the proximal portion 17 of the housing 11. The first lip 49 extends radially inwardly towards the central axis A-A of the housing 11. The first lip 49 extends from the end of the peripheral wall 20 of the proximal portion 17 that is remote to the end wall 21 of the proximal portion 17. The first lip 49 comprises a proximal-facing surface 49A.

The second stop 50 is in the form of a second lip 50 that is integrally formed with the peripheral wall 18 of the distal portion 16. The second lip 50 extends radially outwardly away from the central axis A-A of the housing 11. The second lip 50 extends from the end of the peripheral wall 18 of the distal portion 16 that is remote to the end wall 19 of the distal portion 16. The second lip 50 comprises a distal-facing surface 50A.

Figure 2:
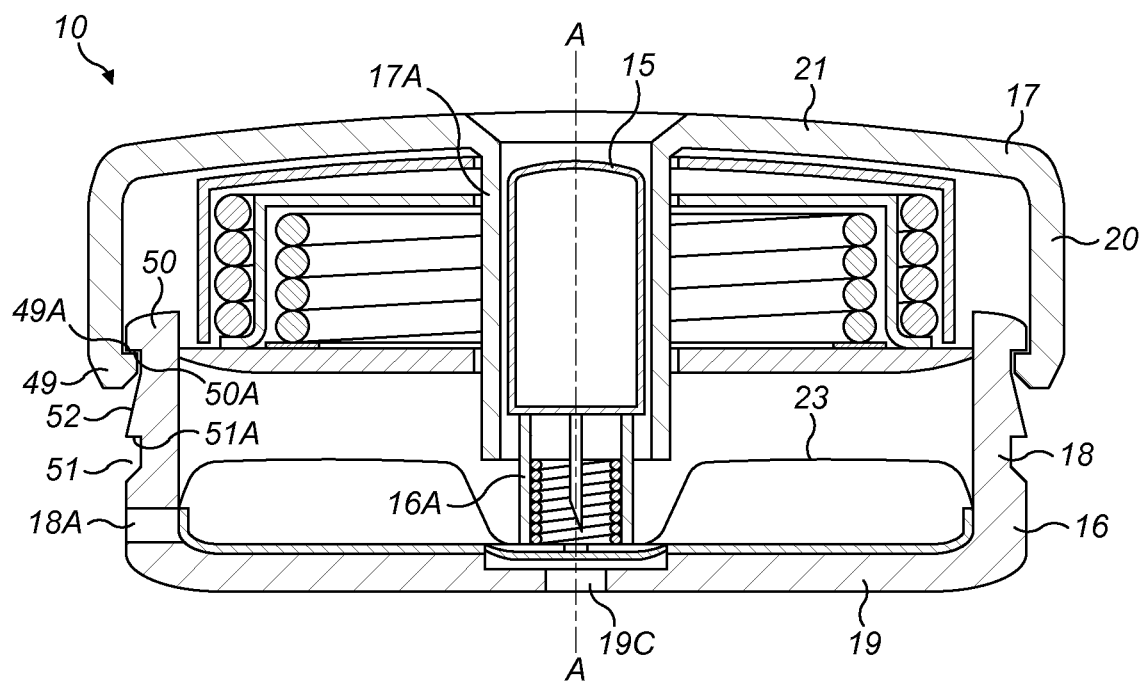
FIG. 2 is a schematic cross-sectional side view of the medicament delivery device of FIG. 1, wherein the proximal portion is in the initial position and the flexible bag is filled with medicament.

When the proximal portion 17 of the housing 11 is in the initial position (as shown in FIGS. 1 and 2), the proximal-facing surface 49A of the first lip 49 abuts the distal-facing surface 50A of the second lip 50 to limit the range of axial movement between the proximal portion 17 and the distal portion 16 such that the proximal portion 17 is prevented from moving away from the distal portion 16 and being separated therefrom.

The third stop 51 is in the form of a recess 51 that extends into the outer surface of the peripheral wall 18 of the distal portion 16. A distal-facing surface 51A is formed at the edge of the recess 51.

The latch 48 further comprises an angled surface 52 that extends between the distal-facing surface 50A of the second stop 50 and the distal-facing surface 51A of the third stop 51. The angled surface 52 is angled slightly with respect to the central axis A-A of the housing 11 such that the angled surface 52 extends slightly away from the central axis A-A of the housing in the direction from the second stop 50 to the third stop 51. The angled surface 52 is formed from a portion of the outer surface of the peripheral wall 18 of the distal portion 16.

The angled surface 52 is configured such that when the proximal portion 17 is moved from the initial position to the primed position the first lip 49 moves over the angled surface 52 and is urged radially outwardly by the angled surface 52 such that the first lip 49 is urged away from the central axis A-A of the housing 11. The thickness and material of the proximal portion 17 is such that when the first lip 49 moves over the angled surface 52 the peripheral wall 20 of the proximal portion 17 resiliently deforms radially outwardly. This flexing of the peripheral wall 20 facilitates movement of the first lip 49 over the angled surface 52. Similarly, the distal portion 16 may also have a thickness and/or be manufactured from a material that allows for the peripheral wall 18 of the distal portion 16 to flex radially inwardly as the first lip 49 moves over the angled surface 52. The distal and proximal portions 16, 17 may be manufactured from, for example, plastic or metal.

Movement of the proximal portion 17 from the initial positon to the primed position causes the first lip 49 to move over the angled surface 52 from the second lip 50 towards the recess 51. When the first lip 49 reaches the recess 51, the first lip 49 moves radially inwardly to 'snap' into the recess 51 such that the proximal-facing surface 49A of the first lip 49 abuts the distal-facing surface 51A at the edge of the recess 51. Thus, the proximal portion 17 is held in place in the primed position such that the end wall 21 of the proximal portion 17 is resisted from moving away from the end wall 19 of the distal portion 16.

The angled surface 52 is arranged to provide a small amount of resistance to the first lip 49 moving over the angled surface 52 from the second lip 50 towards the recess 51, due to the first lip 49 being urged radially outwardly when the proximal portion 17 is moved towards the primed position. Therefore, the patient must overcome a small amount of resistance to move the proximal portion 17 relative to the distal portion 16 from the initial position to the primed position. This reduces the likelihood of the proximal portion 17 being accidentally moved to the primed position.

An exemplary operation of the medicament delivery device 10 will now be described. The medicament delivery device 10 is typically stored in a sterile packaging (not shown). The patient first removes the medicament delivery device 10 from the sterile packaging. When the medicament delivery device 10 is removed from the sterile packaging the proximal portion 17 of the housing 11 is in the initial position, the needle 12 is in the retracted position, the flexible bag 23 is empty, and the button 15 is retracted into the proximal portion 17 (as shown in FIG. 1) such that the patient is not able to access the button 15 to actuate the button 15. For example, the inner dimension of the internal wall 17A of the proximal portion 17 may be sufficiently small that the patient is not able to insert a finger into the internal wall 17A to access the button 15. Thus, the patient is not able to depress the button 15 to operate the dispensing mechanism 14 to dispense medicament from the flexible bag 23 and thus the dispensing mechanism 14 is rendered inoperable. Moreover, the patient is not able to operate the needle actuating mechanism 13 to move the needle 12 to the extended position.

The patient then supplies medicament to the dispensing mechanism 14 of the medicament delivery device 10. More specifically, the patient supplies medicament via the filling port 18A in the peripheral wall 18 of the distal portion 16 of the housing 11 such that the flexible bag 23 is filled with medicament (as shown in FIG. 2). The medicament may be supplied from, for example, a syringe, container, or pressurised canister. In an alternative embodiment, the medicament reservoir 23 is pre-filled with medicament, in which case the filling port 18A may be omitted.

The label (not shown) is then removed from the adhesive layer (not shown) on the outer surface 19A of the end wall 19 of the distal portion 16. The adhesive layer is then adhered to the patient's skin at the injection site such that the end wall 19 of the distal portion 16 is secured to the injection site.

The patient then applies a force to the proximal portion 17 of the housing 11 to move the proximal portion 17 from the initial position to the primed position. For example, the patient may use one hand to apply a force to the outer surface 21A of the distal wall 21 of the proximal portion 17 to push said distal wall 21 towards the distal wall 19 of the distal portion 16. As the proximal portion 17 is moved towards the primed position, the plate 24, first spring 25, second spring 26, internal container 27 and extension member 28 are moved towards the flexible bag 23 until the plate 24 is moved to a first position (shown in FIGS. 3 and 4) wherein the plate 24 abuts the flexible bag 23 or is in close proximity with the flexible bag 23.

When the proximal portion 17 reaches the primed position, the first stop 49 engages with the third stop 51 such that the proximal portion 17 is retained in the primed position.

The first dispensing lock, which is initially in the locked state, holds the first spring 25 in a compressed position between the end wall 27A of the internal container 27 and the proximal-facing surface of the lip 28C of the extension member 28. The first spring 25 biases the plate 24 and extension member 28 away from the end wall 21 of the proximal portion 17 and towards the flexible bag 23.

The second dispensing lock, which is initially in the locked state, holds the second spring 26 in a compressed position between the end wall 28A of the extension member 28 and the proximal-facing surface 24B of the plate 24. The second spring 26 biases the plate 24 away from the extension member 28 and towards the flexible bag 23.

Figure 3:
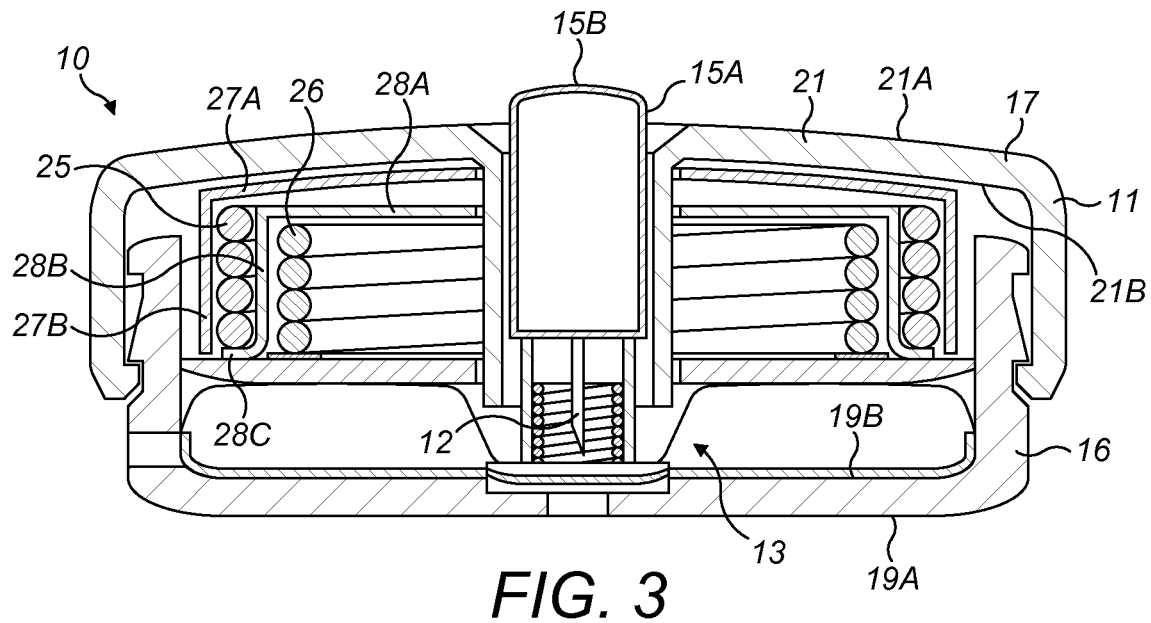
FIG. 3 is a schematic cross-sectional side view of the medicament delivery device of FIG. 1, wherein the proximal portion is in a primed position and a needle is in a retracted position.

The button 15 is slidably received in the internal wall 17A of the proximal portion 17 of the housing 11 such that when the proximal portion 17 is moved to the primed position the button 15 slides relative to the proximal portion 17 to project from the proximal portion 17 (as shown in FIG. 3). Therefore, the button 15 may be actuated by the patient. The button 15 projects from the end wall 21 of the proximal portion 17 when the proximal portion 17 is in the primed position.

Figure 4:
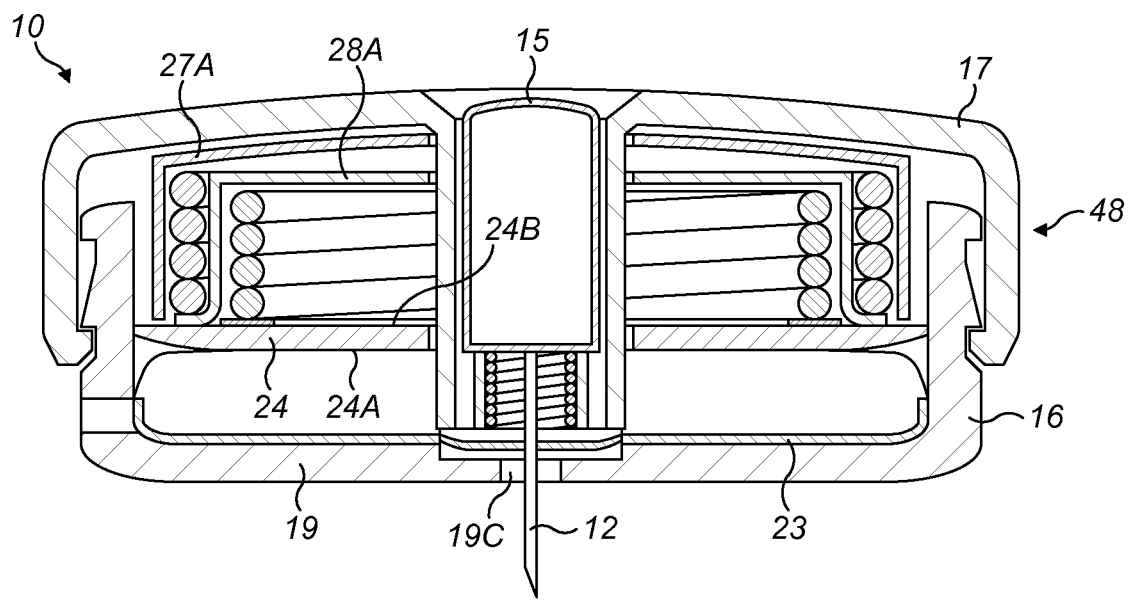
FIG. 4 is a schematic cross-sectional side view of the medicament delivery device of FIG. 1, wherein the proximal portion is in a primed position, a needle is in an extended position and a dispensing member is in a first position.

With the proximal portion 17 in the primed position, the medicament delivery device 10 is primed for supplying medicament to the injection site of the patient. The patient depresses the end wall 15B of the button 15 such that the button 15 is slid into the proximal portion 17 of the housing 11. This causes the button 15 to engage with the needle extension lock 36 such that the needle extension spring 32 is released to move the needle 12 to the extended position. In more detail, the button 15 is moved towards the end wall 19 of the distal portion 16 until the projection 15C of the button 15 is urged against the angled surface 41A of the second projection 41 of the extension locking member 38, resulting in the extension locking member 38 rotating from the locked state to the unlocked state (as shown in FIG. 5). As discussed above, this allows the base 12A of the needle 12 to move away from the extension holding element 34 under the force of the needle extension spring 32 such that the needle 12 moves axially to pass through the septum 31 to extend out of the aperture 19C in the end wall 19 of the distal portion 16. Thus, the needle 12 is moved to the extended position (as shown in FIG. 4). The end wall 19 of the distal portion 16 is adhered to the patient's skin and therefore when the needle 12 is moved to the extended position the needle 12 enters the injection site of the patient.

When the needle 12 is moved to the extended position the needle 12 is fluidly communicated with the inside of the flexible bag 23. In one embodiment, a conduit (not shown) is provided that is fluidly connected to the inside of the flexible bag 23. The needle 12 comprises an aperture (not shown) that aligns with the conduit to fluidly communicate therewith when the needle 12 is moved to the extended position such that medicament is able to flow out of the flexible bag 23, through the conduit, and into the aperture of the needle 12 to be dispensed from the needle 12.

Figure 6:
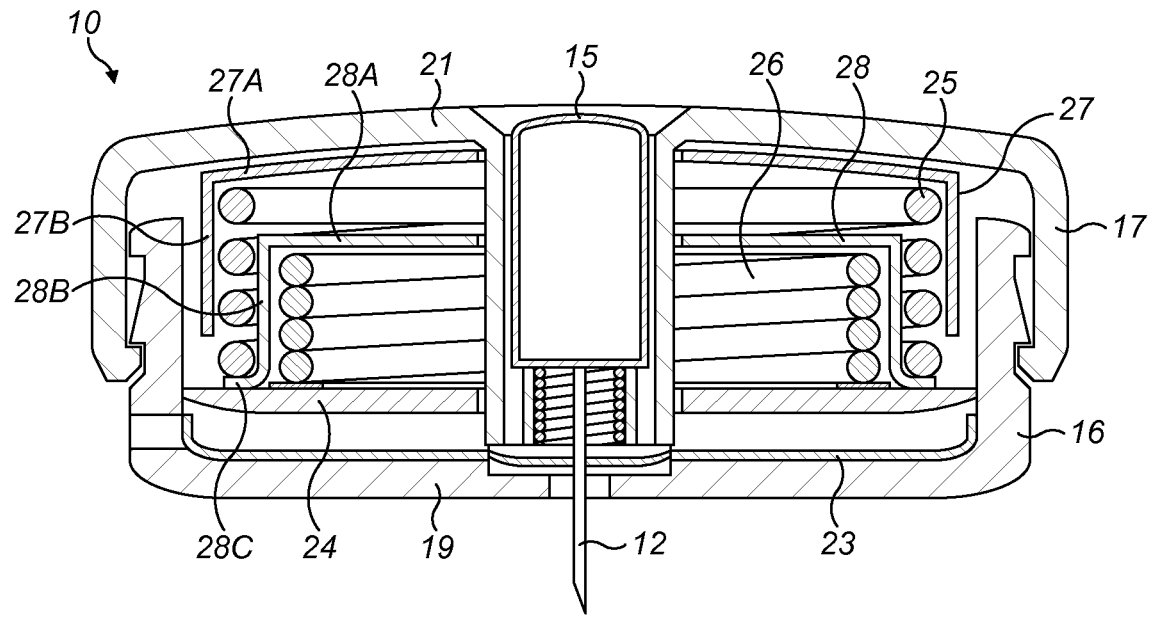
FIG. 6 is a schematic cross-sectional side view of the medicament delivery device of FIG. 1, wherein the dispensing member is in an intermediate position and the needle is in an extended position.

The patient continues to push the button 15 into the housing 11 to then engage the button 15 with the first dispensing lock (not shown) to move the first dispensing lock to the unlocked state. Therefore, once the needle 12 has been moved to the extended position, the first spring 25 is released to urge the extension member 28 away from the end wall 27A of the internal container 27 and towards the end wall 19 of the distal portion 16 in the direction of the central axis A-A of the housing 11. The plate 24 is retained against the extension member 28 by the second dispensing lock and therefore when the extension member 28 is moved by the first spring 25 the plate 24 is also moved towards the end wall 19 of the distal portion 16 to move from the first position to an intermediate position (as shown in FIG. 6) such that medicament is dispensed from the flexible bag 23. More specifically, the flexible bag 23 is compressed between the distal-facing surface 24A of the plate 24 and the inner surface 19B of the end wall 19 of the distal portion 16 such that the pressure of the medicament in the flexible bag 23 is increased and therefore a first volume of medicament flows out of the flexible bag 23 and through the needle 12 to enter the injection site of the patient.

The first spring 25 may extend to a state wherein it is substantially uncompressed when the plate 24 is in the intermediate position. Thus, when the plate 24 is in the intermediate position the plate 24 is not moved any further towards the end wall 19 of the distal portion 16 by the first spring 25.

Figure 7:
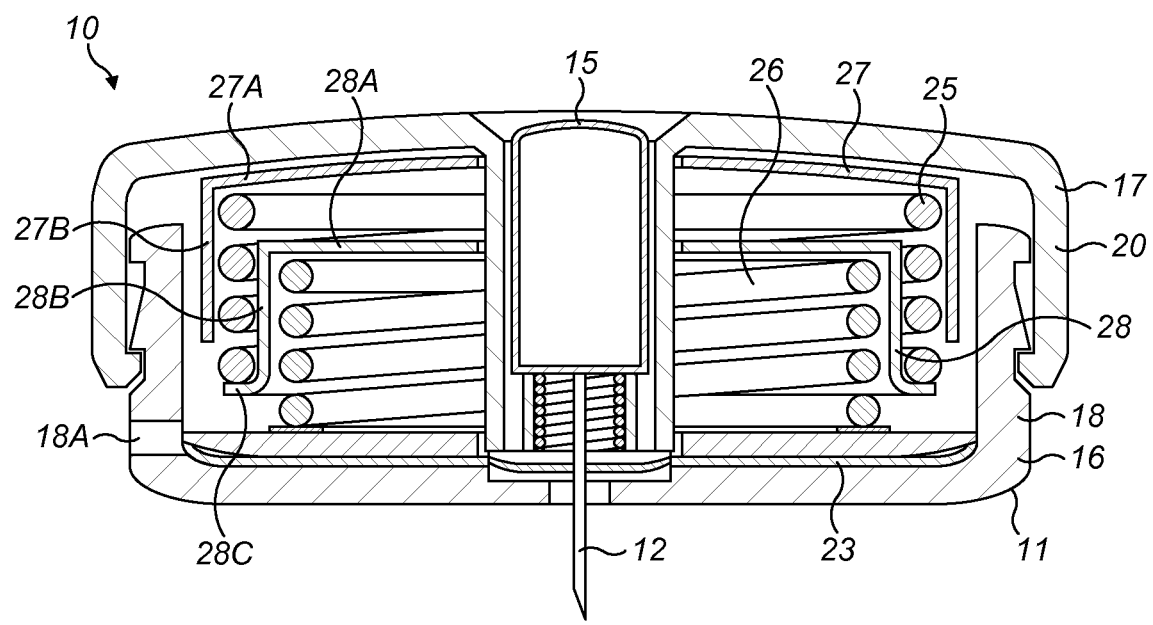
FIG. 7 is a schematic cross-sectional side view of the medicament delivery device of FIG. 1, wherein the dispensing member is in a second position and the needle is in the extended position.
Figure 8:
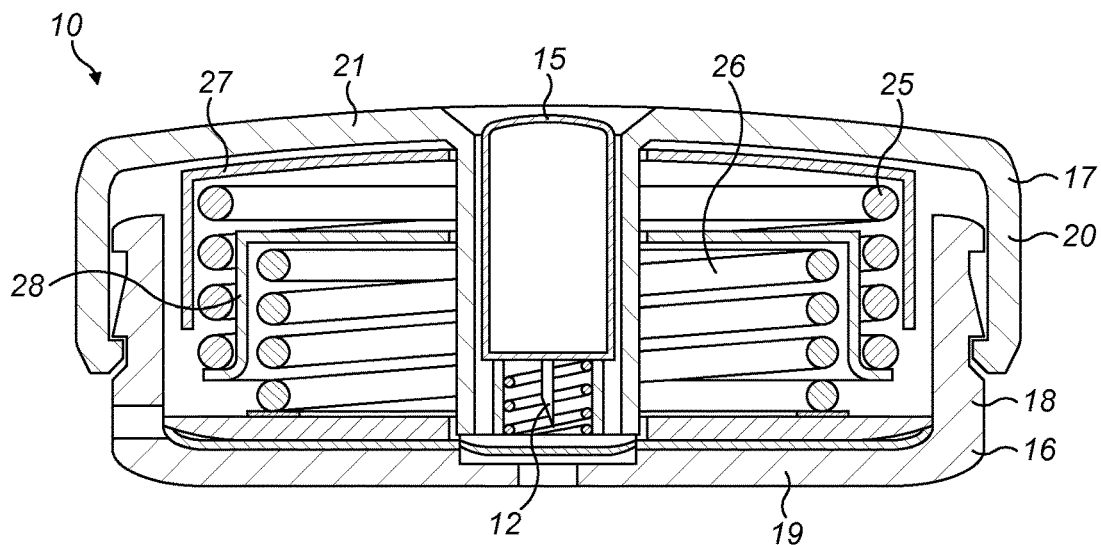
FIG. 8 is a schematic cross-sectional side view of the medicament delivery device of FIG. 1, wherein the dispensing member is in the second position and the needle is in the retracted position.

When the plate 24 reaches the intermediate position, the plate 24 engages with the second dispensing lock (not shown) to move the second dispensing lock to the unlocked state such that the second spring 26 is released to urge the plate 24 away from the extension member 28 and towards the end wall 19 of the distal portion 16. This causes the plate 24 to move relative to the housing 11 from the intermediate position to a second position (as shown in FIGS. 7 and 8) such that further medicament is dispensed from the flexible bag 23. More specifically, the flexible bag 23 is further compressed between the distal-facing surface 24A of the plate 24 and the inner surface 19B of the end wall 19 of the distal portion 16 such that the pressure of the medicament in the flexible bag 23 is increased and therefore a second volume of medicament flows out of the flexible bag 23 and through the needle 12 to enter the injection site of the patient.

When the plate 24 is in the second position, the second spring 26 may extend telescopically out of the first spring 25. The first spring 25 is located on a first side of the extension member 28 and the second spring 26 is located on a second side of the extension member 28. More specifically, the distal end of the first spring 25 abuts the lip 28C on the first side of the extension member 28 and the second spring 26 abuts the end wall 28A on the second side of the extension member 28.

Once the button 15 has been depressed such that the first dispensing lock is moved to the unlocked state to commence medicament delivery, the patient may stop pressing the button 15.

The plate 24 will continue to move towards the end wall 19 of the distal portion 16 under the force of the first spring 25 and then the second spring 26 such that the flexible bag 23 is compressed and thus medicament is delivered to the injection site of the patient via the needle 12. Therefore, the medicament delivery device 10 may be used to deliver medicament to the injection site of the patient over an extended time period, for example, several hours, without requiring the patient to continuously apply a force to the button 15.

Medicament will continue to be delivered to the injection site until the plate 24 moves to the second position within the housing 11, at which point the plate 24 engages with the needle retraction lock 37 such that the needle retraction spring 33 is released to move the needle 12 to the retracted position. In more detail, the plate 24 is moved towards the end wall 19 of the distal portion 16 under the force of the first spring 25 and then the second spring 26 until the plate 24 is urged against the free end 44A of the first elongate member 44 of the retraction locking member 42, resulting in the retraction locking member 42 rotating from the locked state (shown in FIG. 9A) to the unlocked state (shown in FIG. 9B). As discussed above, this allows the retraction holding element 35 to move away from the end wall 19 of the distal portion 16 under the force of the needle retraction spring 33 such that the retraction holding element 35 is urged against the base 12A of the needle 12 to move the needle 12 into the housing 11 to the retracted position (as shown in FIGS. 8 and 9B). The patient may then remove the medicament delivery device 10 from the injection site.

In one embodiment the first spring 25 has a different spring constant to the second spring 26. Therefore, the flow rate of medicament delivered to the injection site when the plate 24 is moved from the first position to the intermediate position is different to the flow rate when the plate 24 is moved from the intermediate position to the second position.

In one embodiment (not shown), an actuator lock may be provided to lock the button 15 in position when the proximal portion 17 is in the initial positon. The actuator lock may comprise an actuator locking member that is in a locked state when the proximal portion 17 is in the initial position to prevent movement of the button 15 relative to the housing 11. The actuator locking member is moved to an unlocked state when the proximal portion 17 is moved to the primed position such that the button 15 can be moved relative to the housing 11.

In one embodiment, the first dispensing lock (not shown) comprises a locking member that is rotatably mounted to the internal wall 17A of the proximal portion 17. When the first dispensing lock is the locked state, part of the locking member engages with the end wall 28A of the extension member 28 to retain the extension member 28 in position relative to the proximal portion 17 such that the first spring 25 in held in a compressed position between the end wall 27A of the internal container 27 and the proximal-facing surface of the lip 28C of the extension member 28. An end of the locking member of the first dispensing lock extends through an aperture in the internal wall 17A of the proximal portion 17. When the button 15 is pushed into the housing 11 the button 15 engages with said end of the locking member to urge the locking member to rotate out of engagement with the extension member 28. Thus, the first dispensing lock is rotated from the locked state to the unlocked state such that the extension member 28 is able to move relative to the proximal portion 17 to move away from the end wall 27A of the inner container 27. In one embodiment, the locking member of the first dispensing lock is biased into engagement with the extension member 28 by a spring, for example, a torsional spring, such that the first dispensing lock is biased into the locked state. When the button 15 is pressed into the housing 11 the button 15 exerts a force on the locking member that overcomes the biasing force of said spring to move the first dispensing lock to the unlocked state.

In an alternative embodiment, the first dispensing lock (not shown) comprises a first projection that is fixed relative to the internal wall 17A of the proximal portion 17 and a second projection that is fixed relative to the end wall 28A of the extension member 28. Initially, the first and second projections engage to axially retain the extension member 28 in position relative to the proximal portion 17 such that the first spring 25 in held in a compressed position between the end wall 27A of the internal container 27 and the proximal-facing surface of the lip 28C of the extension member 28.

The button 15 comprises a cam surface. When the button 15 is pushed into the housing 11, the cam surface engages with the second projection of the extension member 28 to urge the extension member 28 to rotate such that the second projection is moved out of engagement with the first projection of the proximal portion 17 and thus the extension member 28 is no longer axially constrained. Therefore, the first dispensing lock is moved from the locked state to the unlocked state such that the extension member 28 is able to move relative to the proximal portion 17 to move away from the end wall 27A of the inner container 27.

In yet another embodiment, the first dispensing lock (not shown) comprises an electrically operated latch. The electrically operated latch initially holds the extension member 28 in position relative to the proximal portion 17 of the housing 11. The electrically operated latch may be operated to release the extension member 28 such that the extension member 28 is able to move relative to the proximal portion 17 to move away from the end wall 27A of the inner container 27. In one such embodiment, the first dispensing lock comprises a switch that is operated when the button 15 is pressed into the housing 11 to operate the electrically operated latch. The electrically operated latch may be an electromagnetic latch.

In another embodiment (not shown), the first dispensing lock is omitted. Instead, the plate 24 is held in the first position due to the presence of medicament in the medicament reservoir 23, which is initially sealed. When the button 15 is pressed into the housing 11 the needle 12 moves to the extended position and is fluidly communicated with the medicament reservoir 23 such that medicament flows out of the medicament reservoir 23 as the plate 24 moves away from the first position under the force of the first spring 25.

In one embodiment, the second dispensing lock comprises a locking member (not shown) that is rotatably mounted to the end wall 28A of the extension member 28. The locking member is located proximate the internal wall 17A of the proximal portion 17 and extends longitudinally in the direction of the central axis A-A of the housing 11 through the central aperture in the annular plate 24. The locking member has a projection that initially engages with the distal-facing surface 24A of the plate 24 such the plate 24 is held axially in abutment with the extension member 28 against the force of the second spring 26. The locking member is biased to rotate towards the central axis A-A of the housing 11 to move the projection out of engagement with the plate 24 such that the second spring 26 is released to urge the plate 24 away from the extension member 28 and towards the end wall 19 of the distal portion 16. The locking member may be biased by a biasing member, for example, a torsional spring or a helical spring which is located in the central aperture of the plate 24. The locking member initially abuts the internal wall 17A of the proximal portion 17 such that the locking member is prevented from rotating out of engagement with the plate 24. However, when the plate moves to the second position, the locking member aligns with a recess (not shown) in the internal wall 17A of the proximal portion 17 such that the locking member moves into the recess under the force of the biasing member, and thus the projection moves out of engagement with the plate 24. Therefore, when the plate 24 reaches the intermediate positon the second dispensing lock moves from the locked state to the unlocked state to allow the plate 24 to move axially away from the extension member 28.

In an alternative embodiment, the second dispensing lock (not shown) comprises a locking member that extends from the end wall 28A of the extension member 28. The locking member is located proximate the internal wall 17A of the proximal portion 17 and extends longitudinally in the direction of the central axis A-A of the housing 11 through the central aperture in the annular plate 24. The locking member has a projection that extends radially outwardly and initially engages with the distal-facing surface 24A of the plate 24 such the plate 24 is held in abutment with the extension member 28 against the force of the second spring 26. The plate 24 comprises a projection that engages with a cam surface of the proximal portion 17 of the housing 11 when the plate 24 reaches the intermediate position such that the plate 24 rotates about the central axis A-A of the housing 11. This causes the projection of the locking member to align with a slot in the plate 24 such that the projection no longer holds the plate 24 axially in position relative to the extension member 28. Therefore, when the plate 24 reaches the intermediate positon the plate 24 rotates such that the second dispensing lock moves from the locked state to the unlocked state to allow the projection of the locking member to pass through the slot such that the plate 24 moves away from the extension member 28.

In yet another embodiment, the second dispensing lock (not shown) comprises an electrically operated latch. The electrically operated latch initially holds the extension member 28 in position relative to the plate 24 to prevent the plate 24 and extension member 28 from moving apart. The electrically operated latch may be operated to release the plate 24 when the plate 24 reaches the intermediate position such that the plate 24 is able to move away from extension member 28 to move to the second position. In one such embodiment, the second dispensing lock comprises a switch that is operated when the plate 24 reaches the intermediate position to operate the electrically operated latch. In one embodiment, the switch is mounted to the distal portion 16 of the housing 11. The electrically operated latch may be an electromagnetic latch.

In an alternative embodiment, the second dispensing lock is omitted. In one such embodiment, the biasing force generated by the first spring 25 is greater than the biasing force generated by the second spring 26 such that the first spring 25 extends to move the plate 24 to the intermediate position and then the second spring 26 extends to move the plate 24 from the intermediate position to the second position. In one such embodiment, the first spring 25 is fully extended when the plate 24 is in the intermediate position.

In further alternative embodiments (not shown), the first dispensing lock engages with the first spring 25 to retain the first spring 25 in a cocked position when the first dispensing lock is in the locked state and/or the second dispensing lock engages with the second spring 26 to retain the second spring 26 in a cocked position when the second dispensing lock is in the locked state.

Referring now to FIGS. 10 to 16, a medicament delivery device 60 according to a second embodiment of the disclosure is shown. The medicament delivery device 60 of the second embodiment of the disclosure is similar to the medicament delivery device 10 of the first embodiment, with like features retaining the same reference numerals. A difference is that the medicament delivery mechanism of the medicament delivery device 10 of the first embodiment is omitted and is replaced with an alternative medicament delivery mechanism.

The medicament delivery mechanism of the second embodiment comprises a housing 61, a needle 62, a medicament reservoir 63, a dispensing member 64, and first and second biasing members 65, 66.

The housing 61 and needle 62 are similar to the housing 11 and needle 12 of the first embodiment of the disclosure and so a detailed description will not be repeated hereinafter. The housing 61 comprises a distal portion 16 and a proximal portion 17 that is moveable relative to the distal portion 16 between initial and primed positions. The needle 62 is movable relative to the housing 61 between a retracted position (shown in FIGS. 11, 12 and 16), wherein the needle 62 is fully received within the housing 61, to an extended position (shown in FIGS. 13 to 15), wherein the needle 62 projects from the end wall 19 of the distal portion 16 of the housing 61.

The medicament reservoir 63 is in the form of an annular flexible bag 63 that is disposed in the housing 61. The flexible bag 63 is pre-filled with medicament prior to being located in the recess 22 in the housing 61.

The dispensing member 64 is in the form of a plate 64. The plate 64 is disposed in the recess 22 in the housing 61 such that the flexible bag 63 is located between a distal-facing surface 64A of the plate 64 and the inner surface 19B of the end wall 19 of the distal portion 16.

The first and second biasing members 65, 66 are in the form of respective first and second springs 65, 66. The first spring 65 and/or second spring 66 may be a helical spring.

The medicament delivery mechanism further comprises a first lock 67, a second lock (not shown) and an extension member 68.

The extension member 68 is disposed in the recess 22 in the housing 61 and is moveable relative to the housing 61 in the direction of the central axis A-A of the housing 61.

The extension member 28 comprises an end wall 28A, a peripheral wall 28B and a lip 28C. The end wall 68A of the extension member 68 is spaced from the lip 68C in the direction of the central axis A-A of the housing 61 such that the end wall 68A is located nearer than the lip 68C to the end wall 21 of the proximal portion 17. The end wall 68A extends radially inwardly towards the internal wall 17A of the proximal portion 17 from the proximal end of the peripheral wall 68B. The lip 68C extends radially outwardly from the distal end of the peripheral wall 68B of the extension member 68. A distal-facing surface of the lip 68C abuts the plate 64.

The first spring 65 is disposed in the recess 22 in the housing 61 on the opposite side of the plate 64 to the flexible bag 63. The first spring 65 is located between the peripheral wall 20 of the proximal portion 17 and the peripheral wall 68B of the extension member 68. A proximal end of the first spring 65 abuts the end wall 21 of the proximal portion 17 and a distal end abuts a proximal-facing surface of the lip 68C. Thus, the first spring 65 is configured to urge the extension member 68 away from the end wall 21 of the proximal portion 17 such that the extension member 68 is urged towards the end wall 19 of the distal portion 16.

The second spring 66 is disposed in the recess 22 in the housing 61 on the opposite side of the plate 64 to the flexible bag 63. The second spring 66 is located between the peripheral wall 68B of the extension member 68 and the internal wall 17A of the proximal portion 17. Thus, initially, the second spring 66 may be located inside the first spring 65. A proximal end of the second spring 66 abuts the end wall 68A of the extension member 68 and a distal end abuts a proximal-facing surface 64B of the plate 64. Thus, the second spring 66 is configured to urge the plate 64 away from the end wall 68A of the extension member 68 such that the plate 64 is urged towards the end wall 19 of the distal portion 16.

The first lock 67 is moveable from a locked state to an unlocked state. When the first lock 67 is in the locked state, the needle 62, plate 64 and extension member 68 are fixed relative to the proximal portion 17 of the housing 61 in the direction of the central axis A-A of the housing 61. When the first lock 67 is in the unlocked state, the plate 64 and extension member 68 are able to move away from the end wall 21 of the proximal portion 17 in the direction of the central axis A-A of the housing 61 and the needle 62 is able to move from the retracted position to the extended position.

The first lock 67 comprises a pair of elongate locking members 69 and pivotal couplings 70. The locking members 69 comprise a first end 69A and a second end 69B. The first end 69A of each locking member 69 is rotatably coupled to the proximal portion 17 by a respective pivotal coupling 70. The second end 69B is located nearer to the end wall 21 of the proximal portion 17 than the first end 69A.

Each locking member 69 comprises a recess 71 and an angled surface 72. Each recess 71 is located between the first and second ends 69A, 69B of the respective locking member 69. Each recess 71 is configured to receive a portion of the plate 64 when the lock 67 is in the locked state such that the plate 64 abuts the locking member 69 and thus the plate 64 is held in position relative to the locking member 69 in the direction of the central axis A-A of the housing 61.

The angled surface 72 of each locking member 69 is located at the second end 69B of the respective locking member 69.

When the first lock 67 is in the locked state, the locking members 69 may extend substantially parallel to the central axis A-A of the housing 61 and each angled surface 72 may extend at an angle away from the central axis A-A of the housing 61 and towards the end wall 21 of the proximal portion 17. The angled surfaces 72 are configured such that when the button 15 is pushed into the proximal portion 17, an annular projection 15C at the distal end of the button 15 is urged against the angled surfaces 72. This causes the angled surfaces 72 to be urged towards the central axis A-A of the housing 61 and therefore the locking members rotate 69 towards the central axis A-A such that the first lock 67 moves from the locked state to the unlocked state.

When the first lock 67 moves to the unlocked state the locking members 69 are moved away from the plate 64 such that the plate 64 is no longer received in the recesses 71. Therefore, the plate 64 is able to move relative to the housing 61 in the direction of the central axis A-A.

The second lock is moveable from a locked state to an unlocked state. When the second lock is in the locked state, the plate 64 is fixed relative to the extension member 68 in the direction of the central axis A-A of the housing 61 such that the plate 64 is held against the distal-facing surface of the lip 68C. When the second lock is in the unlocked state, the plate 64 is able to move away from the end wall 68A of the extension member 68 in the direction of the central axis A-A of the housing 61 such that the plate 64 is spaced from the extension member 68.

In some embodiments, the second lock is of a similar arrangement to the variants of the second dispensing lock described above in relation to the medicament delivery device 10 of FIGS. 1 to 9. For example, in one embodiment the second lock (not shown) comprises a locking member that extends from the end wall 68A of the extension member 68. The locking member extends longitudinally in the direction of the central axis A-A of the housing 61 through the central aperture in the annular plate 64. The locking member has a projection that initially engages with the distal-facing surface 64A of the plate 64 such the plate 64 is held in abutment with the extension member 68 against the force of the second spring 66. The plate 64 comprises a projection that engages with a cam member upstanding from the end wall 19 of the distal portion 16 when the plate 64 reaches the intermediate position such that the plate 64 is urged to rotate about the central axis A-A of the housing 61. In one embodiment, the cam member (not shown) comprises a projection with an angled cam surface. This rotation of the plate 64 causes the projection of the locking member to align with a slot in the plate 64 such that the projection no longer holds the plate 64 axially in position relative to the extension member 68. Therefore, when the plate 64 reaches the intermediate positon the plate 64 rotates such that the projection of the locking member passes axially through the slot and thus the second dispensing lock moves from the locked state to the unlocked state to allow the plate 64 to move away from the extension member 68. In another embodiment (not shown), the second lock engages with the second spring 66 to retain the second spring 66 in a compressed position until the second lock is moved to the unlocked state. In one embodiment (not shown), the second lock comprises an electrically operated latch.

The medicament delivery mechanism further comprises needle retraction lock 73 that has a needle retraction spring 74, a retraction holding element 75 and a pair of retraction locking members (not shown). The needle retraction lock 73 is similar to the needle retraction lock 37 of the medicament delivery device 10 of the first embodiment of the disclosure. A difference is that the retraction locking members of the medicament delivery device 60 of the second embodiment are rotatably attached to the flexible bag 63 instead of the distal portion 16 of the housing 61. Thus, when the needle retraction lock 73 is in the locked state movement of the flexible bag 63 in the direction of the central axis A-A of the housing 61 causes a corresponding displacement of the needle 62. Therefore, when the proximal portion 17 is moved from the initial position to the primed position such that the flexible bag 63 and plate 64 are moved towards the end wall 19 of the distal portion 16, the needle 62 is also moved towards the end wall 19 of the distal portion 16.

When the needle retraction lock 73 is in the locked state and the flexible bag 23 abuts the end wall 19 of the distal portion 16 the needle 62 projects out of the end wall 19 such that the needle 62 is in the extended position. Movement of the needle retraction lock 73 to the unlocked state releases the needle retraction spring 74 to exert a force on the needle 72 such that the needle 72 is moved to the retracted position within the housing 61.

Figure 10:
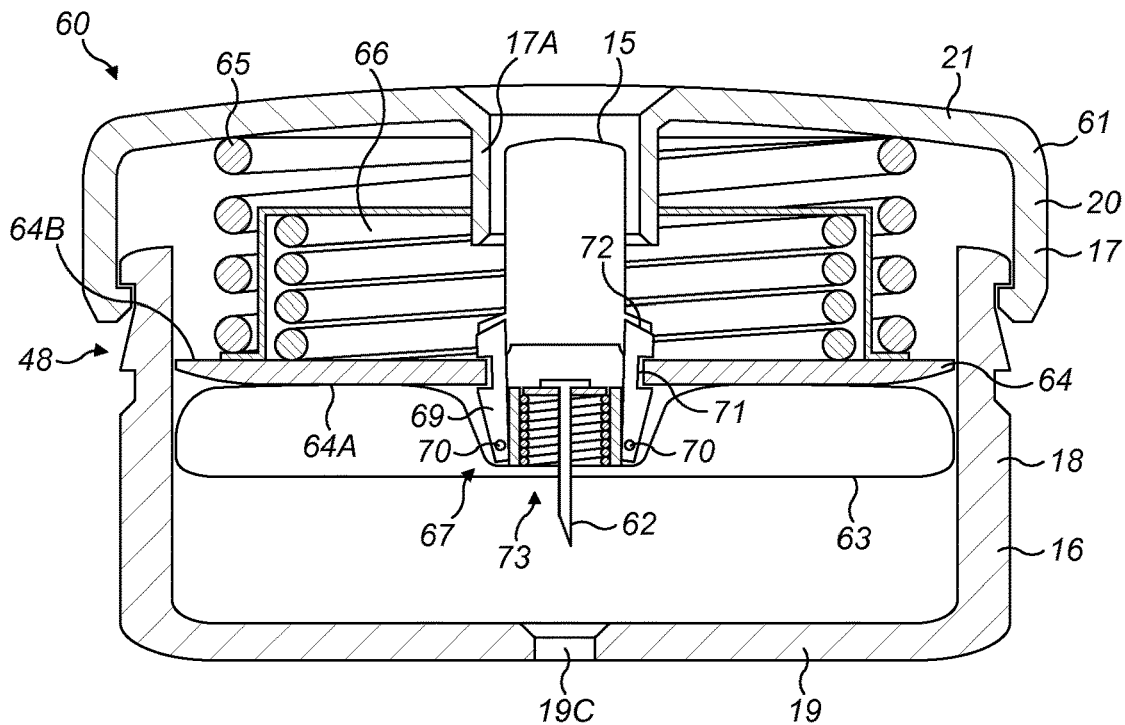
FIG. 10 is a schematic cross-sectional side view of a medicament delivery device according to a second embodiment of the disclosure, wherein a proximal portion of the housing is in an initial position.

An exemplary operation of the medicament delivery device 60 will now be described. The medicament delivery device 60 is typically stored in a sterile packaging (not shown). The patient first removes the medicament delivery device 60 from the sterile packaging. When the medicament delivery device 60 is removed from the sterile packaging the proximal portion 17 of the housing 61 is in the initial position, the needle 62 is in the retracted position, and the button 15 is retracted into the proximal portion 17 (as shown in FIG. 10) such that the patient is not able to access the button 15 to actuate the button 15. Thus, the patient is not able to depress the button 15 to dispense medicament from the flexible bag 63 or move the needle 12 to the extended position.

The patient then supplies medicament to the flexible bag 63 of the medicament delivery device 60, removes the label (not shown) from the adhesive layer (not shown), and adheres the adhesive layer to the patient's skin such that the end wall 19 of the distal portion 16 is secured to the injection site.

The patient then applies a force to the proximal portion 17 of the housing 11 to move the proximal portion 17 from the initial position to the primed position. As the proximal portion 17 is moved towards the primed position, the needle 62, plate 64, first and second springs 65, 66, and extension member 68 are moved towards the flexible bag 63 until the plate 64 is moved to a first position (shown in FIG. 11) wherein the plate 64 abuts the flexible bag 23 which is spaced from the end wall 19 of the distal portion 16.

When the proximal portion 17 reaches the primed position, the latch 48 retains the proximal portion 17 in the primed position.

The first lock 67, which is initially in the locked state, holds the first spring 65 in a compressed position between the end wall 21 of the proximal portion 17 and the proximal-facing surface of the lip 68C of the extension member 68. The first spring 65 biases the plate 64 and extension member 68 away from the end wall 21 of the proximal portion 17.

The second lock, which is initially in the locked state, holds the second spring 66 in a compressed position between the end wall 68A of the extension member 68 and the proximal-facing surface 64B of the plate 64. The second spring 66 biases the plate 64 away from the extension member 68.

Figure 11:
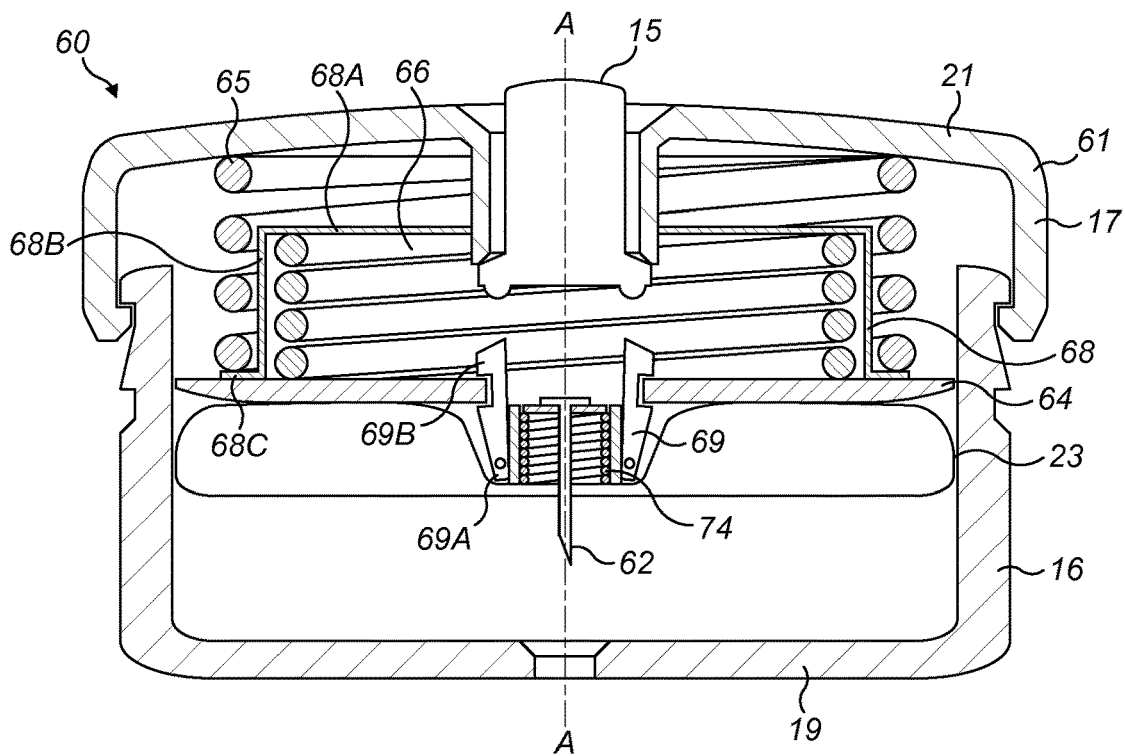
FIG. 11 is a schematic cross-sectional side view of the medicament delivery of FIG. 10, wherein the proximal portion of the housing is in a primed position.

The button 15 is slidably received in the internal wall 17A of the proximal portion 17 of the housing 61 such that when the proximal portion 17 is moved to the primed position the button 15 slides relative to the proximal portion 17 to project from the proximal portion 17 (as shown in FIG. 11). Therefore, the button 15 may be actuated by the patient. The button 15 projects from the end wall 21 of the proximal portion 17 when the proximal portion 17 is in the primed position.

Figure 13:
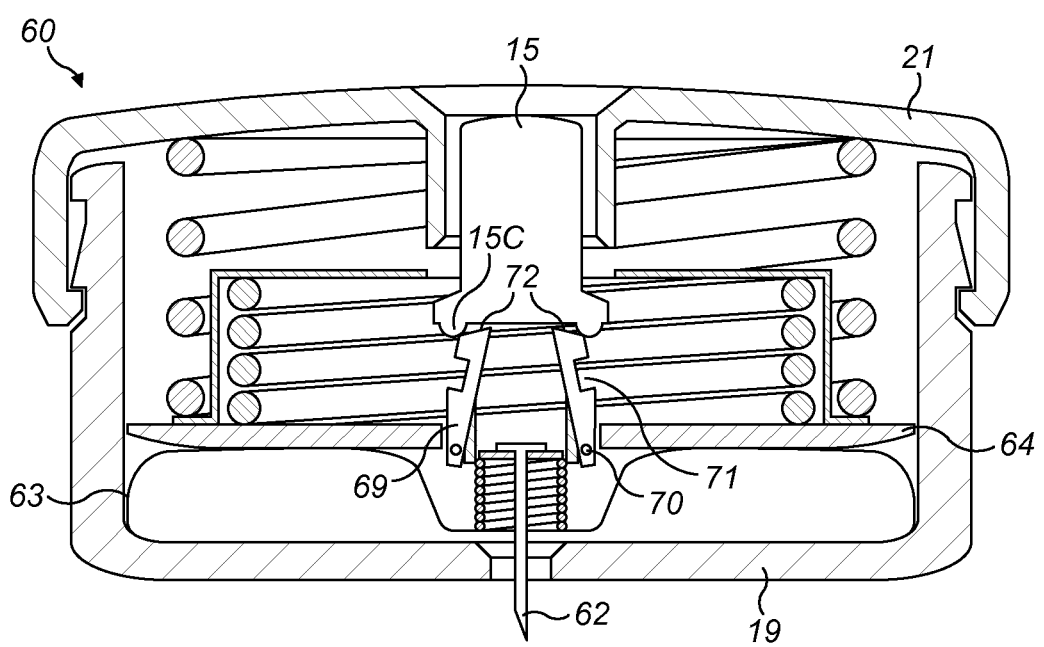
FIG. 13 is a schematic cross-sectional side view of the medicament delivery of FIG. 10, wherein a first biasing means is released.

With the proximal portion 17 in the primed position, the medicament delivery device 60 is primed for supplying medicament to the injection site of the patient. The patient depresses the end wall 15B of the button 15 such that the button 15 is slid into the proximal portion 17 of the housing 11. This causes the button 15 to engage with the first lock 67 such that the first spring 65 is released to move the needle 62, plate 64 and flexible bag 63 towards the end wall 19 of the distal portion 16. Therefore, the flexible bag 63 moves to abut the end wall 19 of the distal portion 16 and thus the needle 62 moves to the extended position (as shown in FIG. 13).

Figure 12:
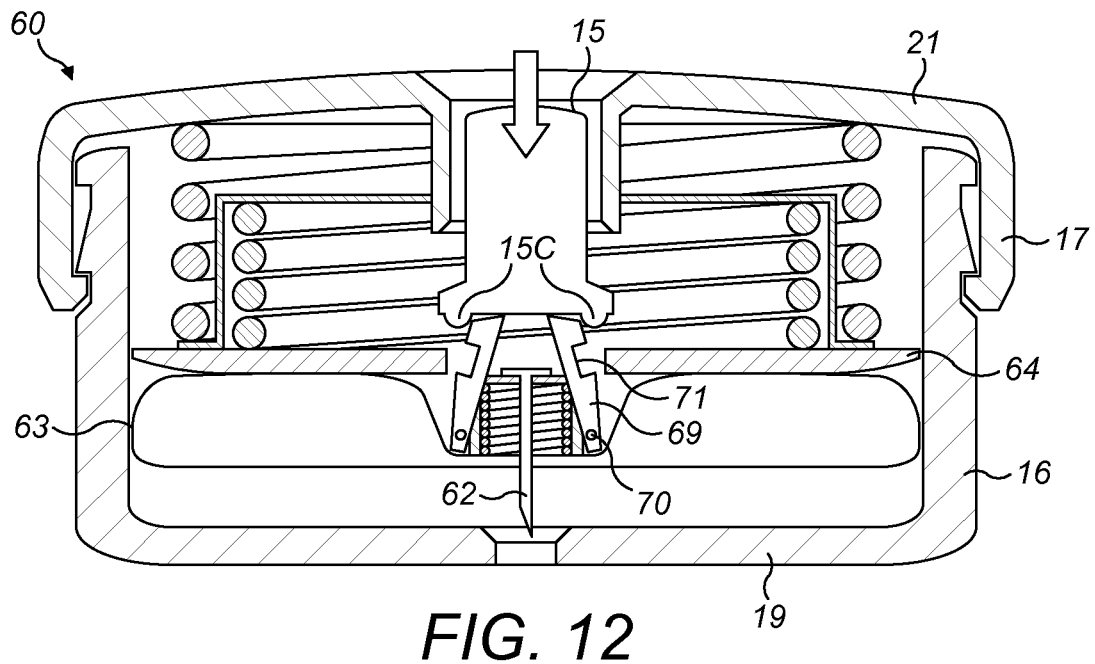
FIG. 12 is a schematic cross-sectional side view of the medicament delivery of FIG. 10, wherein the proximal portion of the housing is in a primed position and an actuator is pressed into the housing.

In more detail, the projection 15C of the button 15 is urged against the angled surfaces 72 of the locking members 69 such that the locking members 69 are rotated towards the central axis A-A of the housing 61 and thus the first lock 67 is moved from the locked state (shown in FIG. 11) to the unlocked state (shown in FIG. 12). As discussed above, this allows the extension member 68 to move away from the end wall 21 of the proximal portion 17 such that the plate 64 is moved from the first position towards the end wall 19 of the distal portion 16 under the force of first spring 65 and thus the needle 62 is moved axially to pass through the septum 31 to extend out of the aperture 19C in the end wall 19. Therefore, the needle 62 is moved to the extended position (as shown in FIG. 13). The end wall 19 of the distal portion 16 is adhered to the patient's skin and therefore when the needle 62 is moved to the extended position the needle 62 enters the injection site of the patient.

Figure 14:
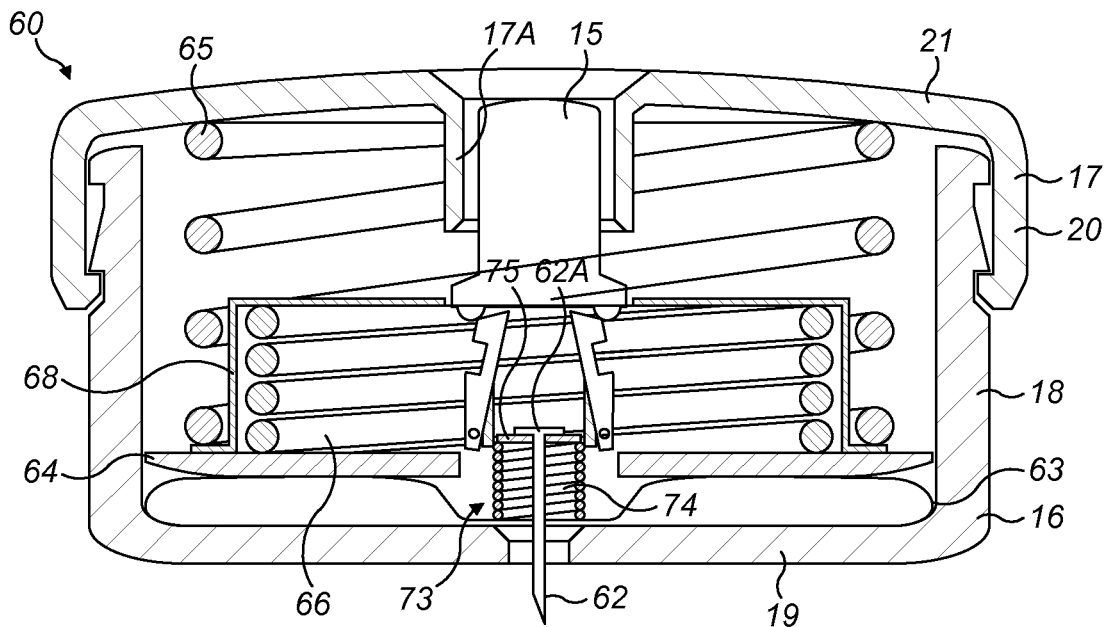
FIG. 14 is a schematic cross-sectional side view of the medicament delivery of FIG. 10, wherein a dispensing member moves to an intermediate position.

When the needle 62 reaches the extended position, the flexible bag 63 abuts the end wall 19 of the distal portion 16 such that the flexible bag 63 is compressed between the end wall 19 and the plate 64, which is urged towards the end wall 19 by the force of the first spring 65 acting on the extension member 68 such that the plate 64 moves from the first position (shown in FIG. 11) to an intermediate position (shown in FIG. 14). Therefore, after the needle 62 has been moved to the extended position medicament is dispensed from the flexible bag 63 and flows through the needle 62 to the injection site of the patient.

Figure 15:
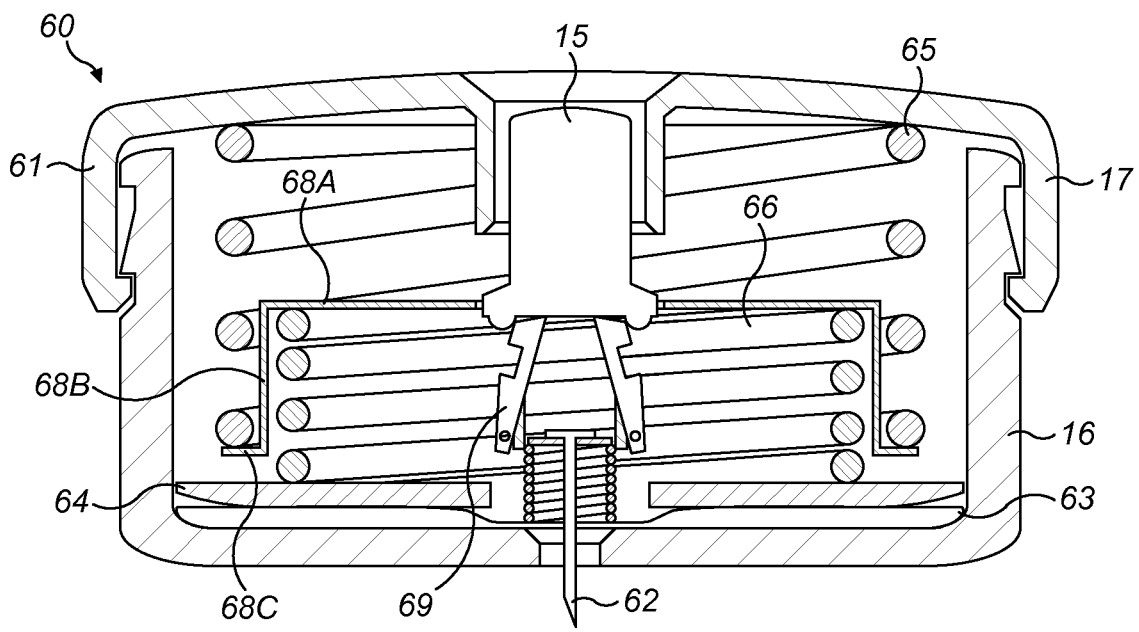
FIG. 15 is a schematic cross-sectional side view of the medicament delivery of FIG. 10, wherein a second biasing means is released, the dispensing member moves to a second position, and a needle is in an extended position.
Figure 16:
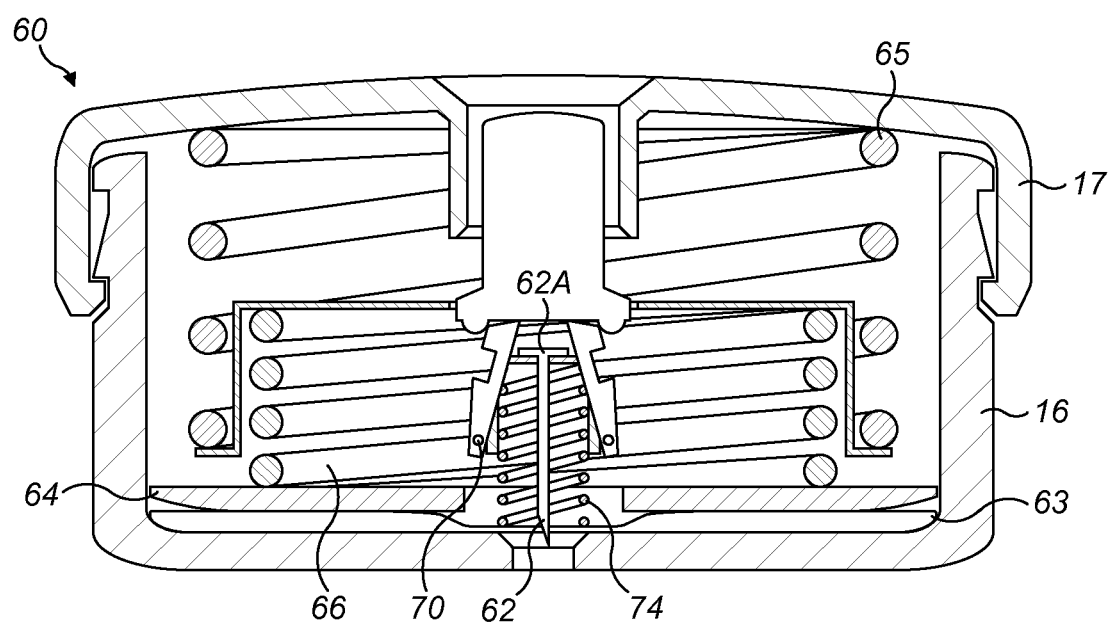
FIG. 16 is a schematic cross-sectional side view of the medicament delivery of FIG. 10, wherein the dispensing member is in the second position and the needle is in a retracted position.

When the plate 64 reaches the intermediate position, the plate 64 engages with the second lock (not shown) to move the second lock to the unlocked state such that the second spring 66 is released to urge the plate 64 away from the extension member 68 and towards the end wall 19 of the distal portion 16. This causes the plate 64 to move relative to the housing 61 from the intermediate position to a second position (as shown in FIGS. 15 and 16) such that further medicament is dispensed from the flexible bag 63. When the plate 64 is in the second position, the second spring 66 may extend telescopically out of the first spring 65.

Once the button 15 has been depressed to the extent that the first lock is moved to the unlocked state to commence medicament delivery, the patient may stop pressing the button 15. The plate 64 will continue to move towards the end wall 19 of the distal portion 16 under the force of the first spring 65 and then the second spring 66 such that the flexible bag 63 is compressed and thus medicament is delivered to the injection site of the patient via the needle 12.

Medicament will continue to be delivered to the injection site until the plate 64 moves to the second position within the housing 61, at which point the plate 64 engages with the needle retraction lock 73 such that the needle retraction spring 74 is released to move the needle 72 to the retracted position. For example, in one embodiment the plate 64 is moved towards the end wall 19 of the distal portion 16 under the force of the first spring 65 and then the second spring 66 until the plate 64 is urged against the retraction locking member, resulting in the retraction locking member rotating away from the retraction holding element 75. This allows the retraction holding element 75 to move away from the end wall 19 of the distal portion 16 under the force of the needle retraction spring 74 such that the retraction holding element 75 is urged against a base 72A of the needle 72 to move the needle 72 into the housing 61 to the retracted position (as shown in FIG. 16). The patient may then remove the medicament delivery device 60 from the injection site.

In the above described embodiment the actuator 15 is fully received within the housing 11, 61 when the proximal portion 17 is in the initial position. However, in an alternative embodiment, the actuator 15 is configured to project from the proximal portion 17 of the housing 11, 61 when the proximal portion 17 is in the initial and primed positions. In one such embodiment, the actuator 15 is of sufficient length to project from the end wall 21 of the proximal portion 17 when the proximal portion 17 is in the initial position.

In the above described embodiment, the first and second dispensing biasing member 25, 65, 26, 66 and the needle extension and retraction biasing members 32, 33 comprise respective springs 25, 65, 26, 66. However, in alternative embodiments (not shown) one or more of the first biasing member 25, 65, second biasing member 26, 66, the needle extension biasing member 32 and the needle retraction biasing member 33 comprise a different type of biasing member, for example, a portion of resiliently deformable material that is compressed to exert a biasing force.

In the above described embodiment, the medicament delivery device 10, 60 comprises a latch 48 that allows for the proximal portion 17 to be moved relative to the distal portion 16. However, in an alternative embodiment (not shown) the latch is omitted and instead the distal and proximal portions 16, 17 comprise respective screw threads. The screw threads engage such that the proximal portion 17 of the housing 11, 61 can be screwed to the distal portion 16 such that the end wall 21 of the proximal portion 17 moves towards the end wall 19 of the distal portion 16. In one such embodiment, a first screw thread is provided on the outer surface of the peripheral wall 18 of the distal portion 16 and a second screw thread is provided on the inner surface of the peripheral wall 20 of the proximal portion 17. In another embodiment, the distal and proximal portions 16, 17 of the housing 11, 61 are fixed relative to each other, and may be integrally formed.

In the above described embodiment, the first and second locks (not shown) are mechanically operated to allow the dispensing member 24, 64 to move from the first position to the intermediate position and then from the intermediate position to the second position. However, in an alternative embodiment (not shown) the first and second locks are instead electrically operated. For example, the first and second locks may comprise respective first and second electromagnetic latches (not shown). The first electromagnetic latch holds the extension member 28, 68 in position relative to the proximal portion 17 and the second electromagnetic latch holds the plate 24, 64 in position relative to the extension member 28, 68. When the button 15 is depressed by the patient the first electromagnetic latch changes state such that the extension member 28, 68 is released to move towards the end wall 19 of the distal portion 16 under the force of the first dispensing spring 25, 65. When the plate 24, 64 reaches the intermediate position the second electromagnetic latch changes state such that the plate 24, 64 moves away from the extension member 28, 68 under the force of the second dispensing spring 26, 66. Similarly, the needle actuating mechanism 13 may instead be electrically operated, for example, comprising a motor (not shown) that moves the needle 12, 62 between the retracted and extended positions.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A medicament delivery device comprising:
    a housing;
    a reservoir for medicament disposed in the housing, the reservoir comprising a collapsible container;
    a dispensing member that is moveable relative to the housing from a first position to a second position to dispense medicament from the reservoir when the reservoir contains medicament;
    a first biasing member configured to urge the dispensing member from the first position to an intermediate position to dispense medicament from the reservoir; and
    a second biasing member configured to urge the dispensing member from the intermediate position to the second position to dispense medicament from the reservoir;
    wherein a needle is movable from a retracted position, in which the needle is fully disposed within the housing, to an extended position, in which the needle projects from the housing, and wherein movement of the dispensing member from the first position to the intermediate position moves the needle from the retracted position to the extended position.

2. A medicament delivery device according to claim 1, wherein the first and second biasing members share a common axis.

3. A medicament delivery device according to claim 1, wherein the first and/or second biasing member comprises a spring.

4. A medicament delivery device according to claim 3, wherein the first and second biasing members comprise springs having different spring constants.

5. A medicament delivery device according to claim 1, further comprising a first lock moveable from a locked state to an unlocked state to allow movement of the dispensing member from the first position to the intermediate position and a second lock moveable from a locked state to an unlocked state to allow movement of the dispensing member from the intermediate position to the second position.

6. A medicament delivery device according to claim 5, wherein the second lock is configured such that movement of the dispensing member from the first position to the intermediate position causes the second lock to move to the unlocked state.

7. A medicament delivery device according to claim 1, wherein the second biasing member is displaced relative to the first biasing member in a direction of motion of the dispensing member when the dispensing member moves from the first position to the intermediate position.

8. A medicament delivery device according to claim 1, wherein the first and second biasing members are telescopically arranged within the housing.

9. A medicament delivery device according to claim 1, further comprising an extension member, wherein the second biasing member is disposed between a first side of the extension member and the dispensing member, and wherein the first biasing member is disposed on a second side of the extension member.

10. A medicament delivery device according to claim 9, wherein the first biasing member is configured to exert a force on the second side of the extension member to urge the dispensing member from the first position to the intermediate position.

11. A medicament delivery device according to claim 9, wherein the extension member is urged against the dispensing member to move the dispensing member from the first position to the intermediate position.

12. A medicament delivery device according to claim 1, wherein the dispensing member is moveable relative to the housing from the first position to the intermediate position to dispense medicament from the reservoir and is movable from the intermediate position to the second position to dispense further medicament from the reservoir when the reservoir contains medicament.

13. A medicament delivery device according to claim 1, wherein the collapsible container comprises a flexible bag.

14. A medicament delivery device according to claim 1, wherein the dispensing member comprises a flat plate.

15. A medicament delivery device according to claim 1, wherein the dispensing member comprises first and second sides, wherein the first and second biasing members are disposed on the first side of the dispensing member and the reservoir is disposed on the second side of the dispensing member.

16. A medicament delivery device according to claim 1, wherein the reservoir contains medicament.

17. A method of dispensing medicament from a medicament delivery device that has a housing, a reservoir disposed in the housing, a needle coupled to a dispensing member, and first and second biasing members, the method comprising:

releasing the first biasing member to exert a force on the dispensing member to move the dispensing member from a first position to an intermediate position to dispel medicament from the reservoir, wherein movement of the dispensing member from the first position to the intermediate position moves the needle from a retracted position, in which the needle is fully disposed within the housing, to an extended position, in which the needle projects from the housing; and, then, releasing the second biasing member to exert a force on the dispensing member to move the dispensing member from the intermediate position to a second position to dispel medicament from the reservoir, wherein the reservoir comprises a collapsible container.

* * * * *